(12) United States Patent
Hougaard et al.

(10) Patent No.: US 11,446,430 B2
(45) Date of Patent: Sep. 20, 2022

(54) CATHETER, A COUPLING COMPONENT FOR COUPLING THE CATHETER TO TUBES, AN APPARATUS INCLUDING THE RECTAL CATHETER, AND A METHOD OF MANUFACTURING THE CATHETER

(71) Applicant: MBH-INTERNATIONAL A/S, Allerød (DK)

(72) Inventors: Ole Hougaard, Helsingør (DK); Cathrine Ørsnes Due, Holte (DK); Henrik Bork Bjerregaard, Brønshøj (DK)

(73) Assignee: MBH-INTERNATIONAL A/S, Allerod (DK)

( * ) Notice: Subject to any disclaimer, the term of this patent is extended or adjusted under 35 U.S.C. 154(b) by 0 days.

(21) Appl. No.: 16/384,837

(22) Filed: Apr. 15, 2019

(65) Prior Publication Data

US 2019/0231969 A1    Aug. 1, 2019

Related U.S. Application Data

(63) Continuation of application No. PCT/DK2017/050338, filed on Oct. 12, 2017.

(30) Foreign Application Priority Data

Oct. 12, 2017    (DK) .......................... PA 2016 70846

(51) Int. Cl.
*A61M 3/02*    (2006.01)
*A61M 25/00*    (2006.01)
(Continued)

(52) U.S. Cl.
CPC ........ *A61M 3/0295* (2013.01); *A61M 3/0279* (2013.01); *A61M 25/0009* (2013.01);
(Continued)

(58) Field of Classification Search
CPC .......... A61M 3/0295; A61M 25/10181; A61M 2210/1067; A61M 2210/1475;
(Continued)

(56) References Cited

U.S. PATENT DOCUMENTS 3,065,750 A * 11/1962 Mandell .............. A61M 3/0295
604/84
5,074,842 A    12/1991 Clayton
(Continued)

FOREIGN PATENT DOCUMENTS

EP    1 531 885 B1    10/2008
GB    2527278 A    12/2015
(Continued)

OTHER PUBLICATIONS

International Search Report and Written Opinion, Appl. No. PCT/DK2017/050338, dated Jan. 25, 2018.
(Continued)

*Primary Examiner* — Lauren P Farrar
*Assistant Examiner* — Hamza A Darb
(74) *Attorney, Agent, or Firm* — Fox Rothschild LLP

(57) ABSTRACT

A catheter for use with an injection apparatus, preferably for rectal irrigation. The catheter has a main body with a funnel-shaped part delimited by an annular funnel wall which tapers into an elongate tubular catheter part delimited by an annular catheter wall. The main body accommodates at least a liquid flow channel and a fluid flow channel and the liquid flow channel is adapted to expel a liquid via at least one injection opening in a free end of the elongate tubular catheter part opposite the funnel-shaped part. An expandable balloon surrounds an elongate fixation section of the elongate tubular catheter part a distance from its free end, and the fluid flow channel is adapted to, via at least one delivery opening provided in the annular catheter wall of the elongate
(Continued)

fixation section of the elongate tubular catheter part, deliver a fluid to the expandable balloon.

29 Claims, 13 Drawing Sheets

(51) Int. Cl.
    *A61M 25/10*     (2013.01)
    *A61M 39/10*     (2006.01)
    *A61M 25/04*     (2006.01)
    *A61B 17/00*     (2006.01)
    *B29C 45/16*     (2006.01)

(52) U.S. Cl.
    CPC .... *A61M 25/10181* (2013.11); *A61M 39/105* (2013.01); *A61B 2017/00526* (2013.01); *A61M 3/022* (2014.02); *A61M 3/0208* (2014.02); *A61M 3/0262* (2013.01); *A61M 25/04* (2013.01); *A61M 2025/0073* (2013.01); *A61M 2039/1016* (2013.01); *A61M 2207/00* (2013.01); *A61M 2210/1064* (2013.01); *A61M 2210/1067* (2013.01)

(58) Field of Classification Search
    CPC .... A61M 2210/1092; A61M 2210/104; A61M 2025/0073; A61M 3/0279; A61M 3/0262; A61M 39/105; A61M 2039/1016; A61M 2207/00; A61M 25/0009; A61M 3/0208; A61M 3/022; A61M 25/1025; A61M 39/00; A61M 25/10; A61M 2025/0004; A62M 25/04; A62M 2210/1089; A61B 2017/00526; B29C 45/1676
    See application file for complete search history.

(56) References Cited

U.S. PATENT DOCUMENTS

| | | | |
|---|---|---|---|
| 2003/0060799 A1* | 3/2003 | Arenberg | A61F 11/00 604/514 |
| 2012/0143168 A1* | 6/2012 | Bjerregaard | A61M 3/0295 604/514 |
| 2013/0099476 A1* | 4/2013 | Chevereau | A61M 3/0279 285/123.12 |
| 2014/0155864 A1* | 6/2014 | Andreen | A61M 3/0258 604/514 |
| 2014/0276662 A1* | 9/2014 | Douglas | A61M 25/007 604/544 |
| 2016/0128755 A1* | 5/2016 | Ho | A61B 18/042 606/41 |
| 2019/0358435 A1* | 11/2019 | Andersin | A61M 25/0111 |

FOREIGN PATENT DOCUMENTS

| | | |
|---|---|---|
| WO | 2011/012323 A1 | 2/2011 |
| WO | 2011/023196 A1 | 3/2011 |
| WO | 2011/160834 A1 | 12/2011 |
| WO | 2013/004236 A1 | 1/2013 |
| WO | 2013/182593 A1 | 12/2013 |
| WO | 2014/154635 A1 | 10/2014 |
| WO | 2016/007536 A1 | 1/2016 |

OTHER PUBLICATIONS

Written Opinion of the International Preliminary Examining Authority, Appl. No. PCT/DK2017/050338, dated Aug. 16, 2018.
International Preliminary Report on Patentability, Appl. No. PCT/DK2017/050338, dated Dec. 18, 2018.

* cited by examiner

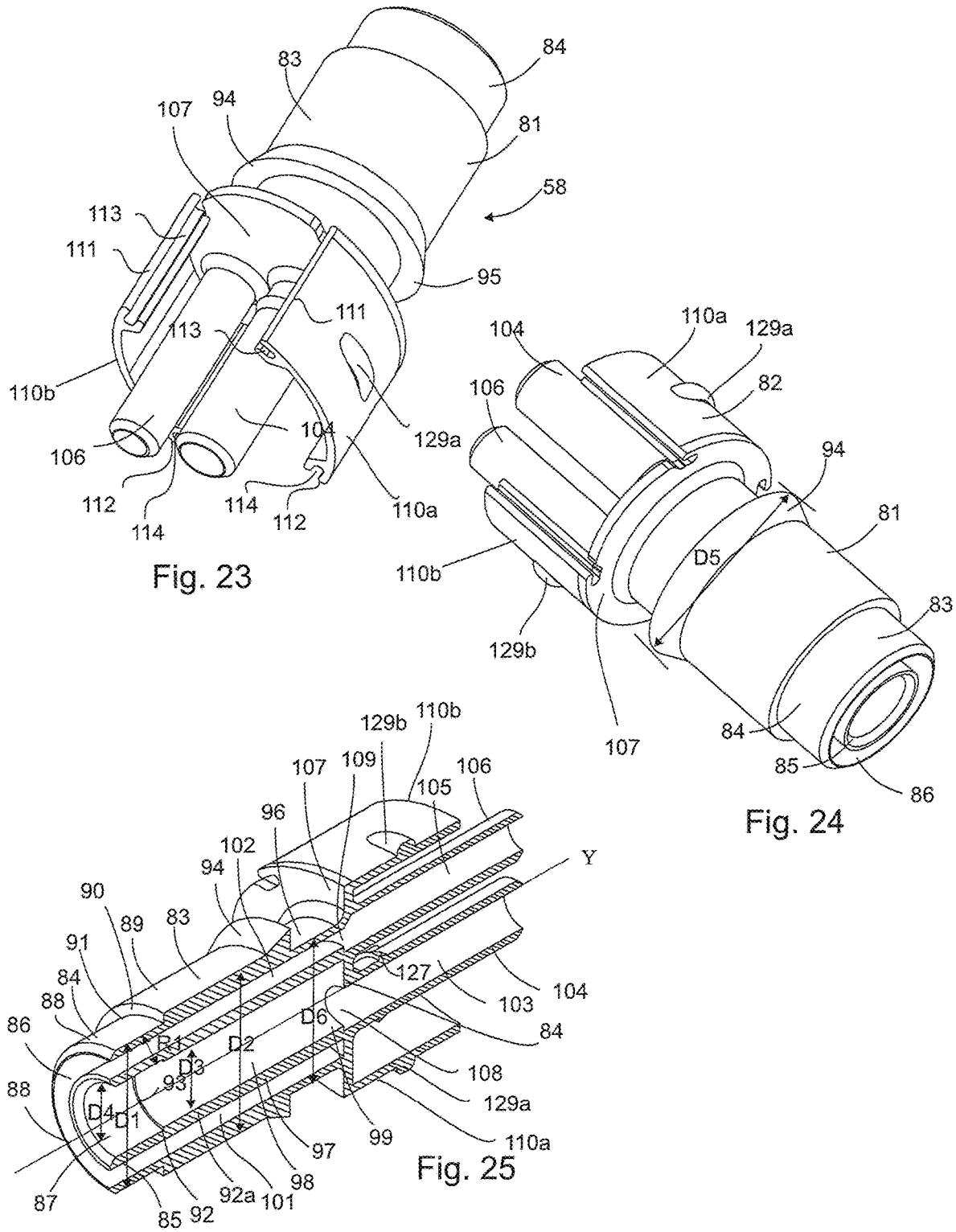

CATHETER, A COUPLING COMPONENT FOR COUPLING THE CATHETER TO TUBES, AN APPARATUS INCLUDING THE RECTAL CATHETER, AND A METHOD OF MANUFACTURING THE CATHETER

CROSS-REFERENCE TO RELATED APPLICATIONS

This application is a continuation of International patent application PCT/DK2017/050338 filed Oct. 12, 2017 claiming priority of Danish application PA 2016 70486 filed Oct. 28, 2016.

BACKGROUND

The present invention relates to a catheter adapted for injection of a liquid into a body cavity, said catheter being coupled to a coupling component adapted to couple to tubes for establishing fluid communication to an injection liquid reservoir, said catheter has a main body comprising a funnel-shaped part delimited by an annular funnel wall and an elongate tubular catheter part delimited by an annular catheter wall, which funnel-shaped part has a flared part that, via a smooth transition, tapers into a tapering part, which extend into the elongate tubular catheter part, the main body accommodates a liquid flow channel, which is adapted to expel a liquid via at least one injection opening in a free end of the elongate tubular catheter part opposite the funnel-shaped part, wherein the catheter has an expandable fixation member that surrounds an elongate fixation section of the elongate tubular catheter part a distance from the free end of said elongate tubular catheter part, and a fluid flow channel which is adapted to, via at least one delivery opening provided in said annular catheter wall of the elongate fixation section of the elongate tubular catheter part, deliver a fluid to the expandable fixation member.

The present invention concerns in particular the field of devices for performing irrigation and enema, e.g. by injecting liquid via the rectum into the colon, e.g. to motivate evacuation of stool, to relieve constipation, avoid or treat faecal incontinence, or just for cleansing the colon when desired.

Within the context of the present invention the term "body cavity" means a body cavity into which the catheter part of the present invention is inserted for one or more of the purposes of irrigation, cleansing and/or infusion downstream the catheter. Access openings and access channels to the body cavity includes e.g. the anus, however artificial stomas and fistulas can also serve to access a body cavity for the purpose of performing irrigation using an irrigation liquid, cleansing using a cleansing liquid, or infusion using an infusion liquid.

Irrigation involves emptying the lower part of the bowel by slowly introducing e.g. warm tap water, saline and/or laxatives, into the rectum using a catheter held in place with a balloon, similar to a self-retaining catheter. The liquid is introduced into the bowel via the rectal catheter, by a hand-held pump, so patients can control the amount and speed of water entering the bowel. The liquid is subsequently evacuated together with the contents of the rectum, the sigmoid and possibly the descending colon when the balloon is deflated and removed.

Within the context of the present invention the term "liquid" means any substance including a liquid phase, or is a solution or suspension including liquid. Examples of liquids include but are not limited to any conventional irrigation liquid or cleansing liquid, such as the above-mentioned water, saline, and laxative solutions. However, oils, oil/water, or infusions of medicaments are also suitable for injection into the body cavity via a rectal catheter of the present invention.

U.S. Pat. No. 5,074,842 describes an irrigation system, which comprises a tube and an expandable fixation member in form of a balloon for retaining the tube in the rectum during injection. Said balloon can be inflated after the insertion of the tube. The balloon is inflated using air, which is delivered through a syringe valve, which communicates with an air passage. A similar system is known from European patent publication no. 1531885, which describes an irrigation system comprising a liquid reservoir, and an air-inflated balloon for fixation of a tubular part inserted in the rectum.

Even though the balloon in these known systems will assist the patient by helping to keep the tubular part of an irrigation rectal catheter in the correct place inside the rectum during the irrigation, these systems have the major drawback that if the balloon is inflated too much it is harmful to the patient, and if the balloon is inflated too little it cannot safely keep the tube in place during use due to the air-filled balloon reacting to the body movements, e.g. peristaltic reflexes, resulting in that the tube inconveniently may fall out of rectum as well as leakage of injected liquid around the inflated balloon can occur. This is not only unwelcoming for the patient but also very demeaning, as the surroundings inevitability will be contaminated with irrigation liquid and bodily excretions.

Furthermore, since air is used to inflate the balloon in these known systems, additional elements are needed in the systems in order to ensure that the air can be taken from the surroundings and vented to the surroundings instead of into the body cavity when the irrigation is completed. If the air at this stage was delivered to the rectum and/or bowel this would result in an additional distending or dilation resulting in additional pain and discomfort for the patient.

However, air as a means to distend the balloon has the advantage of being easy available from the surroundings, and therefore easy to administer to the balloon. Air flows easily and fast through even very small holes and air as a balloon-distending means does not put heavy demand on the size and shape of the air-delivery opening at the section of the tube surrounded by the balloon. Even small air-delivery openings may suffice and an appropriate number of holes for this purpose are e.g. made after termination of the molding of the rectal catheter by drilling through the annular wall of the catheter part, and then securing the balloon to tightly surround said holes. Making tiny air holes in the wall of the hollow tubular catheter part, e.g. by drilling, does not have a severe impact on the final structural integrity of the catheter part. Larger holes are not needed when using air or gas as distending fluid.

Fluids having higher density, such as e.g. water or saline, however cannot flow easily through these conventional tiny air holes below the balloon. The user needs to apply a very high inflation pressure at the risk of causing unintentional detachment of tubes or hoses and rectal catheter because the liquid will find another way out of the system, as well as it will take considerable time to distend the balloon of the above known irrigation systems with liquid delivered through tiny holes.

European patent applications no. 10747405.8 discloses an irrigation device having a rectal catheter with a balloon that is filled with liquid instead of air. A dual-lumen tube or hose supplies, under the control of a valve member, liquid from a common liquid reservoir via respective dedicated channels of the rectal catheter into either a balloon to be distended to fixate the rectal catheter in the desired location in the rectum, or out of the tip of the rectal catheter and directly into the rectum to irrigate at least a part of the bowel. At this stage the liquid-distended balloon prevents injected liquid from getting out of the body again until the balloon is deflated.

This known rectal catheter is a rigid structure without body conforming or body mimetic shape or properties. The applicant has discovered that to avoid unintended detachment when pumping liquid from the reservoir to the rectal catheter, e.g. when performing a cleansing enema or a retention enema, the sealing between tubes or hoses for delivering liquid from the injection liquid reservoir through the rectal catheter to the body cavity, and optionally to the balloon, and can be improved.

International patent application no. WO2013/004236 discloses another rectal catheter with a balloon element, where the balloon element is provided with ribs under the balloon element so as to prevent the balloon from being attached to the shaft of the catheter to an extent where the balloon is difficult to inflate. The catheter has a lengthwise extending liquid channel(s) used for instillation of the irrigation liquid, and a parallel balloon channel that extend from the distal end and through the shaft of the catheter to terminate in one or more inflation outlets provided under the balloon element. The means for connecting this known catheter does however not conform to anatomical shape and may be difficult to operate due to being hard to reach.

SUMMARY OF THE INVENTION

It is therefore an aspect of the present invention to provide a catheter of the kind mentioned in the opening paragraph that is configured for improved fluid-tight connection to tubes or hoses for supplying liquid from a liquid-reservoir, preferably a common liquid-reservoir, to an expandable fixation member surrounding a catheter part of the catheter, and through one or more injection openings at the free end of the catheter.

It is yet an aspect of the present invention to provide a catheter of the kind mentioned in the opening paragraph that has a structural design conforming to human body anatomy.

It is yet an aspect of the present invention to provide a catheter of the kind mentioned in the opening paragraph that has a main body that can be manufactured in a single injection molding procedure.

It is yet an aspect of the present invention to provide a catheter of the kind mentioned in the opening paragraph that can be used in home-irrigation procedures.

It is yet an aspect of the present invention to provide a rectal catheter of the kind mentioned in the opening paragraph that makes it possible to perform transanal irrigation without soiling the user and the surroundings.

It is yet an aspect of the present invention to provide a catheter of the kind mentioned in the opening paragraph for use in a rectal injection apparatus.

It is yet an aspect of the present invention to provide a catheter of the kind mentioned in the opening paragraph that is inexpensive to manufacture and is simple and reliable to use in an injection apparatus for irrigating and/or cleansing a body cavity.

It is yet an aspect of the present invention to provide a rectal catheter of the kind mentioned in the opening paragraph for use in relieving constipation and faecal incontinence.

It is yet an aspect of the present invention to provide a simple method of manufacturing the catheter.

The novel and unique whereby these and other aspects are achieved according to the present invention consist in that the coupling component is a tube connection component being part of a tube coupling adaptor, which tube coupling adaptor further comprises a catheter connector component and a decoupling component.

Within the context of the present invention the term "flared" "flared part" and "flaring" means that the part so referred to gradually become wider from the elongate tubular catheter part until the free end of the funnel-shaped part, whereby the exterior side of the annular funnel wall is given a concavity of curvature, e.g. a curvature following a hyperbola to define a smooth curve, that results in an exterior curvature of the flared part lying in a plane that conform anatomically to the exterior rectal area at the intergluteal cleft via which the catheter must be manipulated. Thus the tapering part gradually extends into the flared part which becomes wider and wider towards a free end that serves as abutment face to the human body during use.

So the funnel-shaped part is the part of the catheter that is left outside the body when the elongate tubular catheter part is arranged in its irrigation position in the body cavity, e.g. a transanal irrigation position inside the rectum. The flared part of the funnel-shaped part advantageously prevents the catheter from getting too far inside the body cavity, e.g. too far inside the rectum, and it does not protrude so far from the body during use that it is in the way. The tapering part of the funnel-shaped part serves as a smooth convenient transition into the catheter part. This configuration is not at risk of slipping into the bowel system during irrigation due to the plugging function of the funnel-shaped part.

So the danger that the catheter accidentally detaches from the tubes or hoses that provide liquid communication to a liquid reservoir or any fluid reservoir, and proceeds to move inside the body cavity, e.g. up the intestinal duct, is eliminated. The flared funnel-shaped part simply is too large to allow it to pass through the access opening to the body cavity and slipping further into the access opening, e.g. through the anus and further up the body cavity, as has been reported for straight prior art devices for making enema, e.g. for prior art enema devices having substantially same diameter along the length. Advantageously the curvature of the funnel-shaped part resembles the curvature of the exterior human anatomy around the anus.

While the provision of fluid through a straight double-lumen catheter may be straight forward, the funnel-shaped part of the catheter of the present invention presents a challenge regarding extending the flow channel through the elongate tubular catheter part into the funnel-shaped part. One solution could be to make the funnel-shaped part solid, but this would add considerable weight to the catheter, and the need for extra goods makes the catheter too expensive for throwaway use.

This challenge is solved by the present invention in that the liquid flow channel and the fluid flow channel passes through the main body along the longitudinal axis of said main body, e.g. in the form of elongate bores, pipes or tube, such as co-axial bores, tube and pipes extending from the funnel-shaped part and further inside the main body of the catheter. The liquid flow channel may have at least one injection opening at the free end of the tubular catheter part opposite the funnel-shaped part to allow liquid flowing through said liquid flow channel to be expelled into the body cavity in order to conduct irrigation, cleansing and/or infusion. To provide structural integrity to the liquid flow channel and fluid flow channel they may be joined centrally along at least a part of their length, thus share a lengthwise wall part along or parallel to the elongate axis of the catheter. Preferably the flow channels are lengthwise partially integral and solid with the annular funnel wall and the annular catheter wall, respectively, thus a lengthwise annular section of the annular funnel wall and the annular catheter wall can also constitute annular wall parts of the respective liquid flow channel and fluid flow channel. The liquid flow channel and the fluid flow channel can thus in one embodiment both be at least partly solid with each other and/or with an annular section of the annular wall and an annular section of the funnel wall.

The fluid flow channel serves to deliver a fluid, optionally liquid from the same reservoir as the injection liquid delivered through the liquid flow channel, to an expandable fixation member, such as a balloon, that surrounds at least an elongate fixation section of the tubular catheter part that does not include the at least one injection opening. So the injection opening at the free end of the catheter tip opposite the funnel-shaped part is free of the fixation member. Fluid is delivered to the expandable fixation member via at least one delivery opening provided in the annular wall of the section of the elongate tubular catheter part which is encased by the fixation member and in fluid communication with the fluid flow channel. The fixation member may be secured fluid-tight to said section e.g. by gluing or be heat welded.

Both the at least one injection opening and the at least one delivery opening are sized to provide for an unobstructed and gentle flow of liquid or fluid, respectively, into the respective recipient, the body cavity or the fixation member. In use the fixation member is expanded sufficiently for the catheter to stay properly and firmly inside the body cavity, on the one hand to an extent where the catheter does not pop out in response to the liquid pressure arising when liquid during injection is pumped into the body cavity, and on the other hand to an extent where liquid cannot escape beyond the expanded fixation member during and at the end of injection. When the fluid to be injected into the fixation member is liquid, the tiny air holes, e.g. 1 mm in diameter, for distending balloons of prior art rectal catheters using air, do not allow for a controlled and reasonable liquid flow and liquid injection into the expandable fixation member, such as a balloon. If these prior art rectal catheters were used to inject liquid it would take very long time and at the risk of tubes or hoses detaching, due to back pressure, if e.g. the user gets impatient and applies a too high pump pressure, which will make a positive pressure to build up at the pump side, which positive pressure cannot be relieved any other way than by the tubes or hoses detaching, resulting in that injection liquid is spilled and/or injected liquid flushes back.

When using liquid, such as the injection liquid, as an expansion fluid for the fixation member, such as a balloon, one or a few larger holes instead of a plurality of tiny air holes provide for a smooth injection of liquid into the fixation member.

The size of an injection opening and/or a delivery opening may e.g. be about 50% or more of the cross-section of the corresponding flow channel, optionally 60% or more, alternatively 70% or more, alternatively 80% or more, alternatively 90% or more, or in yet an alternative substantially equal to or larger than the cross-section of the corresponding flow channel taken at the location of the respective opening.

These cross-sections of the corresponding flow channels through the funnel-shaped part may be larger, equal to or smaller than the cross-section of the flow channel through the elongate tubular catheter part. These cross-sections may or may not have different outline throughout the length of the respective flow channel and may taper towards and along the elongate tubular catheter part.

The liquid flow channel and the fluid flow channel may be provided as bores, tubes or pipes integral with or integrated inside the main body. For example, be rigid or semi-rigid tubes or pipes that do not collapse in response to forces applied by the body cavity, such as e.g. the rectal duct.

The liquid flow channel may end in a chamber at the free end of the catheter part, and several injection openings may be provided in the annular wall at the free end of the tubular catheter part, e.g. circumferentially distributed at the free end. However, one or two injection openings may suffice and be appropriate. A preferred embodiment of a catheter of the present invention may have two injection openings.

Although it is beneficial to make a fast fixation of the catheter using large delivery openings for expanding the fixation member by injecting fluid, such as liquid or air, less fluid needs to enter the expandable fixation member than is injected into the body cavity, so the need for plural delivery openings is less prominent, but the larger delivery opening, the faster the delivery of fluid into the fixation member, and the faster the irrigation can start.

Preferably the fluid flow channel can be shorter than the liquid flow channel, so that the fluid can be delivered directly into the fixation member, such as a balloon. The longer liquid flow channel facilitates expelling of liquid directly to the location in front of the expanded fixation member, which expanded fixation member effectively prevents backflow under the injection or infusion of liquid into the body cavity, such as the rectum and any desired part of the lower part of the bowel. How far inside a body cavity, e.g. up into the bowel, the injected liquid can reach, depends on the amount of injected liquid as well as the patient's or user's position.

Any fluid connection between the liquid flow channel and the fluid flow channel remains closed until the catheter shall be removed. In order to remove the catheter the fixation member must be emptied of fluid.

Filling and emptying the fixation member with liquid, as well as injecting liquid into the body cavity, can be done by operating a valve member to open and close for fluid communication to, from and between the fluid flow channel and the liquid flow channel, e.g. using the valve member and pump system disclosed in the applicants European patent applications no. 10747405.8. In order to empty the expanded fixation member a volume of injection liquid inside the expandable fixation member is simply added to the irrigating injection liquid inside the body cavity of the user or patient by connecting the fluid flow channel to the liquid flow channel via the valve member so that this volume of liquid simply is added to the liquid inside the body cavity to be disposed of together with said injected liquid when the patient evacuates his/her intestines. Once the still clean liquid inside the expandable fixation member is set free to flow back to the valve member to be injected via the liquid flow channel into the body cavity the expandable fixation member inherently deflate, often assisted by peristaltic movements, so that the catheter can be retracted unobstructed.

Catheters, such as e.g. rectal catheters, relying on just one internal liquid flow channel do not allow expanding the expandable fixation member by means of liquid, in particular not liquid taken from the one and same reservoir as the injection liquid.

For the purpose of the present invention liquid are the preferred fluid for the temporarily expanding of the expandable fixation member to keep the catheter in fixed position substantially sealed against the wall of the body cavity during performing irrigation, however gases and air can be used instead, provided such a gas source or air source is made available.

At least the exterior face of the tubular catheter part may have a hydrophilic coating to achieve a smooth, substantially friction free insertion of said tubular catheter part. The hydrophilic coating will also absorb and trap minor amounts of injected injection liquid flowing backwards towards the funnel-shaped part to the exterior surroundings, as well as a hydrophilic coating tends to swell to a minor degree to further temporarily fixing of the position of the catheter in relation to the body cavity.

The catheter of the present invention may be configured so that the liquid flow channel can have a first tube connection piece; optionally the first tube connection piece can protrude beyond the funnel-shaped part. The fluid flow channel can have a second tube connection piece; optionally this second tube connection piece can protrude beyond the funnel-shaped part.

The connection pieces serve to facilitate easy mounting of the tubes or hoses that serve to connect the injection liquid reservoir and/or the expansion fluid reservoir to the catheter.

Because the first tube connection piece and the second tube connection piece protrude from the funnel-shaped part these tube connection pieces are easy to locate even during the irrigation process where the catheter is out of sight of a user, e.g. a user making home enema. Such a user can, if he/she desires, perform a tactile inspection by hand during the irrigation process to verify that all connections between components, including the catheter and the tubes or hoses, are tight and otherwise in order. Furthermore, when said connection pieces protrude from the funnel-shaped part they have additional length to ensure safe coupling directly with tubes or hoses, or indirectly via any other interposed adapter or component needed to obtain liquid communication to the associated injection liquid reservoir and/or fluid communication to the expansion fluid reservoir, which expansion fluid reservoir can be the same as the injection liquid reservoir.

Most of the liquid flow channel and the fluid flow channel are hidden inside the main body of the catheter and cannot be seen by eye, except for the tube connection pieces. So in order to assemble the catheter and the injection liquid reservoir into a functional device where the correct tube or hose are connected to the corresponding correct liquid flow channel and fluid flow channel, respectively, at least the first tube connection piece of the liquid flow channel may have a different cross-section than the second tube connection piece of the fluid flow channel. This way distinguishing between the two connection pieces is easy, both visually and tactile, so that correct attachment of tubes or hoses are ensured, and so that a valve system associated with the rectal injection apparatus is able to guide liquid and fluid to the respective correct flow channels, optionally to switch correctly between injection of liquid into the expandable fixation member via the delivery opening, emptying the expandable fixation member of injection liquid into the liquid flow channel, and expelling of liquid through the injection opening at the free end of the elongate catheter part into the rectum and bowel.

In an alternative embodiment none of the first tube connection piece and the second tube connection piece protrudes beyond the funnel-shaped part. Instead said tube connection pieces may be configured as a first coupling means inside the opening of the funnel-shaped part and be made integral, or at least have a structural attachment with the interior face of said funnel-shaped part. The first coupling means may conveniently be configured to couple with a second coupling means mounted on the tubes or hoses, on a coupling component, or on a tube coupling adaptor for establishing, optionally facilitating, enema delivery to the body cavity, and injection liquid or expansion fluid to the expandable fixation member.

Advantageously, in some embodiments at least one of the first tube connection piece or the second tube connection piece may be made of an elastic and/or flexible material, so that said tube connection pieces can self-seal to provide a strong reliable fluid-tight seal around any other rigid member introduced into any of said tube connection pieces. Preferably both the first tube connection piece and the second tube connection piece can be made of an elastic and/or flexible material that is selected to have an elasticity, resiliency and flexibility sufficient to be stretched to pass over another member that is rigid, or is substantially rigid and be able to elastically return towards a relaxed condition due to having an inherent memory-shape. Optionally, an elastic tube connection is still slightly elastically tensioned when coupled around a tubular member, in that the elastic tube connection is dimensioned to not be able to reach a completely relaxed condition in the condition where it is mounted on another member. The elastic tube connection then fits closely and fluid-tight around said tubular member. A suitable material is e.g. silicone, however other elastic materials, such as synthetic rubber, having the required elastic properties can be used. Preferred elastic materials are those suited for 2K and 3K injection molding together with a thermoplastic material or a thermoset.

Making the ratio of diameter to length big in the case of cylindrical injection-molded products is however a challenge. During the injection molding of the catheter of the present invention long thin cores or pins serve to create the liquid flow channel and the fluid flow channel, respectively, along the length of the catheter, but such long and thin cores or pins often cause problems, such as falling over, bending, deflecting and even getting broken by the injection pressure when injection molding. Yet a challenge is that the temperature of the central part of the core or pin often will become high compared to the end, so inner diameter measurement of the intended respective flow channel may vary. If the mold cycle is short and the injection pressure high there is also a risk that the above disadvantages will make the substantial parallel cores or pins for the substantial parallel flow channels to bend towards each other, to even touch each other, so that the flow channels inadvertently are created in fluid communication, a problem which cannot be immediate spotted from outside the catheter. Suitable counter-measures against deformation in an elongate tubular molded product with several flow channels, such as the dual flow channels of the catheter of the present invention, may include to place one or more radial ribs or draw elements towards the circumferential direction to strengthen the stiffness of the core or pin. For example, for the fluid flow channel such opposite stiffening ribs or draw elements may be arranged at the vicinity of the inserted tip of core or pin, and asymmetrically, thus not directly opposite each other in relation to the elongate axis of the rectal catheter.

The elastic tube connections can simply be pushed onto another member in the liquid or fluid line to establish liquid connection to the reservoir of injection liquid and fluid connection to the reservoir of expansion fluid.

A further advantage is that an elastic tube connection automatically conforms to various shapes. So manufacturing tolerances of members to which the rectal catheter is to be coupled is not a problem, as well as the catheter can be used with a variety of diameters and cross-sections of different other components and members required to operatively connect the catheter to the injection liquid reservoir and the expansion fluid reservoir, respectively, which reservoirs both may be the injection liquid reservoir. In a manufacturing process where tolerances are less critical less demand is on the precision of the manufacturing process of both the catheter and any other components of an injection apparatus using the catheter of the present invention. Manufacturing costs can be reduced, and accordingly the selling price can also be reduced at the benefit of the consumers.

In the embodiment of a rectal catheter of the present invention that has elastic tube connection pieces rigid fluid connectors, such as barbed hollow plugs, can be plugged into said elastic tube connection pieces to establish liquid communication to the above-mentioned reservoirs. In this embodiment the tube connection pieces may serve as female connection pieces to receive a male component, such as a male fluid flow connector.

In an alternative embodiment of a rectal catheter of the present invention at least one of the first tube connection piece and the second tube connection piece can be rigid to serve as a male coupling means that fits inside a female coupling means associated with the tube and being provided to establish a corresponding required tight and reliable liquid communication to the reservoirs as when using the opposite above-described coupling arrangement with elastic and flexible female tube connection pieces and rigid male coupling component.

The liquid flow channel and the fluid flow channel can be substantial parallel liquid flow channels to avoid turbulence during injections and to make the flow paths the shortest possible.

Optionally at least a lengthwise section of the liquid flow channel can extend inside a lengthwise section of the fluid flow channel, which enables optimizing and utilization of the internal diameter and a large space inside the elongate tubular catheter part for use in liquid transport to the body cavity to be irrigated.

When at least a lengthwise section of the liquid flow channel extends inside a lengthwise section of the fluid flow channel the second tube connection piece can e.g. surround the first tube connection piece. The injection liquid can then be injected into the body cavity via the at least one injection opening in a free end of the elongate tubular catheter part. Opposite the at least one injection opening the first tube connection piece extends lengthwise inside the second tube connection piece and into the funnel-shaped part. Opposite the second tube connection piece the at least one delivery opening of the fluid flow channel is provided at the elongate fixation section of the annular catheter wall to expel fluid into the fixation member.

In an optimum embodiment the liquid flow channel and the fluid flow channel may be co-axial and the liquid flow channel may be longer than the fluid flow channel, thus pass beyond the at least one delivery opening to be free of the fixation member. Optionally at least a length of the liquid flow channel and the fluid flow channel are arranged concentrically or eccentrically.

In embodiments of catheters of the present invention wherein the second tube connection piece is arranged to surround the first tube connecting piece the coupling component may be a tube connection component which is part of a tube coupling adaptor that further comprises a catheter connector component and a decoupling component for releasing the tube connection component from the catheter. The tube coupling adapter enables parallel tubes or hoses to be connected to annularly arranged tube connections pieces of the catheter in order to supply injection liquid to injection opening(s) and fluid to delivery opening(s), which injection opening(s) and delivery opening(s) advantageously are axially offset along the length of the catheter to a.o. leave axial space for the fixation member.

The catheter connector component may have a first catheter connector part end adapted to couple together with the catheter and an opposite second catheter connector part end adapted for coupling together with the tube connection component. For example, the catheter connector component may be provided with circumferentially arranged means, that are provided to axially jut at the first catheter connector part end to engage inside corresponding coupling gaps between spaced apart partition webs arranged around the second tube connection piece of the funnel-shaped part to couple said catheter connector part together with the catheter. The second catheter connector part end may be provided with axially extending flexible legs that may serve to couple to a third embodiment of a coupling component in form of the tube connection component. The partition webs may also serve to keep the second tube connection piece in a selected position and spaced from the first tube connection piece.

Advantageously the tube connection component can have a tubular front end part adapted to couple together with the second catheter connector part end and/or with the first coupling means inside the opening of the funnel-shaped part of the catheter. An opposite tube connecting end part may be adapted to couple with the tubes or hoses that serve to supply injection liquid and/or expansion fluid to the catheter via the tube coupling adapter. The opposite tube connecting end part may further be adapted to couple with a decoupling component whereby the coupling of the individual components of the tube coupling adaptor as well as the tubes or hoses for supplying the injection liquid and/or the expansion fluid becomes reliable in use.

After use of the apparatus the decoupling component can be displaced along the longitudinal axis of the coupling component to release the tube connection component from the catheter connector component by applying a force on the second catheter connector part of the catheter connector component towards the catheter, where after the user can dispose the apparatus and evacuate the body cavity of injected liquid into the toilet.

Advantageously the tubular front end part of the tube connection component can be provided with an exterior tubular coupling piece that surrounds an interior tubular coupling piece to define a flow gap in-between said coupling pieces to mate together with the annularly arranged first tube connection piece and second tube connection piece of the catheter to provide fluid communication to the respective liquid flow channel and fluid flow channel.

Since the two tubes or hoses that are connected to the injection liquid reservoir, optionally also connected to a reservoir of expansion fluid, are not normally arranged in a corresponding surrounding relationship as the tube connection pieces of the third embodiment of a catheter, as described above, redirections of the flow from the side-byside arranged tubes into the annular arranged flow channels, one inside the other, of the catheter is required.

To convert the flow channels through these tubes or hoses into the annularly arranged flow channels of the catheter, thus into annularly arranged first and second flow channels, the tubular front end part of the tube connection component may have similarly annularly arranged tubular connection pieces. The tube connecting end part opposite the tubular front end part may have separate, spaced apart, e.g. parallel, first and second coupling pieces for coupling to the tubes or hoses from the injection liquid reservoir and the expansion fluid reservoir.

Advantageously the tube connection component may have a guide plate member disposed between the tubular front end part and the tube connecting end part. The guide plate member may be provided with appropriate positioned and dimensioned flow openings arranged to direct liquid and fluid, respectively, flowing from the tubes or hoses into the respective first coupling piece and the second coupling piece and into the annularly arranged liquid flow channel and fluid flow channel via the respective third flow channel and fourth flow channel of the third embodiment of a coupling component.

The present invention also relates to an injection apparatus comprising the above-described embodiments of catheters. Especially the present invention also relates to a rectal injection apparatus comprising the above-described catheters as a rectal catheter.

The injection apparatus of the present invention may advantageously further comprise a coupling component for coupling the respective first tube connection piece in liquid communication with an injection liquid reservoir via a respective first tube or hose and for coupling the respective second tube connection piece in fluid communication with an expansion fluid reservoir via a respective second tube or hose.

A valve means and a pump means may be inserted between said tube(s) and said reservoir(s) for pumping injection liquid from the injection liquid reservoir and fluid from the expansion fluid reservoir to the catheter. Optionally the valve means and pump means is of the kind adapted for emptying the expandable fixation member of added injection liquid and transferring said injection liquid via the fluid flow channel into the liquid flow channel and out of the free end of the catheter part into the body cavity.

The various embodiments of a coupling component are examples of the above-mentioned rigid members that can be plugged into the respective elastic and/or flexible first tube connection piece and the elastic and/or flexible second tube connection piece to connect the injection liquid reservoir and the expansion fluid reservoir in case the tubes or hoses cannot be connected directly to the tube connection pieces of the catheter, e.g. because of substantially different shapes of cross-sections or different diameters, despite the elasticity and flexibility of the tube connection pieces. Some embodiments of a coupling component may serve to compensate for differences in design and dimension of non-mating cross-sections of the respective first tube connection piece and the second tube connection piece and the corresponding coupling member of the tubes or hoses needed to establish fluid connection to the injection liquid reservoir and the expansion fluid reservoir, e.g. via a valve means and a pump means.

Within the scope of the present invention the coupling component of the present invention can come in various configurations to fit together with various catheters and coupling members of the tubes or hoses. Features and structure of one embodiment of a coupling component of the present invention can be included in other embodiments.

The coupling component can be provided ready-for-use where it is already fixed to the catheter, or the coupling component can be provided separate and be assembled to the catheter prior to use. Fixing of the coupling component to the catheter can also be achieved by gluing. In yet an alternative embodiment part of, or the entire, coupling component may be made integral with the catheter in the molding process.

A first embodiment of a coupling component may have a first flow connector adapted to fluid-tight fit together with the first tube connection piece and a second flow connector adapted to fluid-tight fit together with the second tube connection piece, preferably none of the tube connection pieces and the flow connectors have a threading, however threadings or barbs are indeed possible to implement on the flow connectors. A tube connection piece is simply pushed and guided over the appropriate flow connector to fit tightly around said flow connector. Once the injection of liquid into the bowel is completed the catheter is taken out and the user empties the bowel the normal way.

A third flow channel may conveniently extend through the coupling component from the first flow connector to a first coupling piece for coupling to the first tube or hose, and a fourth flow channel may extend through the coupling component from the second flow connector to a second coupling piece for coupling to the second tube or hose.

The third flow channel and the fourth flow channel of the coupling component may be straight, or in another embodiment be curved. The user may choose between these options to avail himself/herself of the coupling component that provides the most ergonomic or the most preferred irrigation position and/or irrigation situation, and depending on the chosen embodiment of a catheter.

In the second embodiment of a coupling component of the present invention the third flow channel and the fourth flow channel can thus be curved to provide the first flow connector and the first coupling piece e.g. about 90° in relation to each other, and/or provide the second flow connector and the second coupling piece e.g. about 90° in relation to each other.

The annular catheter wall may have one or more first annular recesses, such as two spaced apart annular recesses, between the delivery opening and the injection openings, and one or more annular recesses, such as two spaced apart annular recesses distal to the delivery opening, thus between said delivery opening and the funnel-shaped part, which annular recesses advantageously may serve to accommodate glue when a fixation member is adhered to the catheter wall. Preferably two annular recesses can be provided on each opposite side of the delivery opening(s) at the elongate fixation section of the elongate tubular catheter part so that the fixation member can be made into a confined expandable chamber on the catheter. Such two annular recesses may be spaced apart to delimit an elongate gluing section to which glue can be applied when the fixation member, such as a balloon, is adhered to the catheter.

Should the amount of glue be too high, or the glue flow two much, the recesses may serve to take up surplus of glue, so that no other parts of the fixation member than the parts above the elongate gluing sections are glued to the catheter wall, thus so that glue does not flow into areas where it must not come, e.g. into the fluid flow channel and the delivery opening(s). The two recesses on opposite sides of the delivery opening(s) and being closest to each other, may additionally have an extra reservoir in form of an annular run-off area for surplus glue. By having recesses on opposite sides of the elongate gluing section any surplus of glue is offered two reservoir options, one on each side of the elongate gluing section, thereby eliminating the risk that applied glue flows towards the delivery opening(s) and towards the injection opening(s), e.g. when a pressure is applied to make the fixation member, the glue and the elongate gluing section get into strong gluing contact. Advantageously the elongate gluing section, and optionally also the run-off areas, can be parallel to the longitudinal axis of the catheter, so that the glue will distribute evenly, e.g. when subjected to a contact force over said elongate gluing section to promote adhesive force. Any surplus of glue will flow into both recesses on opposite sides of said elongate gluing section, e.g. when the above-mentioned contact pressure is applied to the wall of the fixation member to get it to adhere strongly together with the catheter. A gluing section parallel to the longitudinal axis of the catheter will make the glue distribute evenly over the gluing section and evenly into the opposite recesses.

The present invention also relates to a method of manufacturing a catheter for the injection apparatus described above wherein one or both of the catheter and/or the coupling component is made in a single step by 1K injection molding, 2K injection molding or 3K injection molding.

2K injection molding and 3K injection molding are injection molding processes particular suited to make a mold part composed of different plastic material, e.g. combining a thermoplastic material of the main body of the catheter, which main body has integrated appropriate flow channels, with e.g. elastic tube connection pieces, e.g. of silicone, at the ends of said flow channels, to obtain desired elastic coupling properties of said tube connection pieces, and thus combining the non-collapsible property of the flow channels with the elastic properties of the tube connection pieces. Thereby is obtained that these tube connection pieces can adapt to tolerances of other couplings and fit with a variety of coupling diameters when the catheter is in use and coupled to a reservoir of liquid or fluid to be injected via a respective conduit, e.g. a tube, using valve means and pump means. The valve means can preferably be of the kind that can switch between injection liquid flow to the liquid flow channel and injection liquid flow or expansion fluid flow to the fluid flow channel, and put the liquid flow channel and the fluid flow channel in fluid communication.

Thus using multi-component injection molding facilitates combining a hard thermoplastic component with an elastic, and even a super-elastic, plastic component, e.g. made of silicone.

The catheters of the present invention can advantageously be used to replace the catheter described in relation to the applicant's European patent applications no. 10747405.8, and the further components of the irrigation system described in this prior art application can be the same, thus both hand pump and injection liquid reservoir can be the same. Emphasis is made that the catheters of the present invention can be used in and with any other irrigation system where injection liquid is used both to expand an expandable fixation member and to inject liquid to perform irrigation of the bowel, as well as in relation to irrigation systems where the fixation member is expanded by means of air or gas from a reservoir of expansion fluid.

Optionally an additional locking means can be provided between the catheter and the tubes for supplying injection liquid and/or expansion fluid to said catheter.

BRIEF DESCRIPTION OF THE DRAWINGS

The invention will now be described in further details by way of exemplary embodiments with reference to the drawing, in which FIG. 23 is a perspective view of a tube connection component seen from the tube coupling end, FIG. 24 shows the same seen from the opposite end for coupling with the catheter connector component and the catheter, FIG. 25 is a sectional lengthwise view of the tube connection component seen in FIGS. 23 and 24.

DETAILED DESCRIPTION OF THE INVENTION

By way of non-exhaustive examples, the catheters of the present invention are described as a rectal catheter and the body cavity as the rectum. The catheters may however be inserted via a stoma or a fistula to irrigate and/or clean any other part of the bowel.

Furthermore, blow the invention is described by way of example in relation to using the injection liquid as the expansion fluid as well and where the source of injection liquid also serve as the source of the expansion fluid. It should be noted that this example should not be construed as limiting the scope of the present invention, and that within the scope of the present invention gas and air can be supplied as expansion fluid to the fixation member from a separate gas and/or air source.

The first embodiment of a rectal catheter 1 shown in perspective in FIGS. 1-6 is shown without expandable fixation member. It should however be understood that the rectal catheter 1 includes an expandable fixation member, which in the following detailed description is an elastic balloon to be infused with a liquid.

The rectal catheter has a funnel-shaped part 2 that tapers into an elongated catheter part 3. The elongated catheter part 3 has a free end 4 opposite the funnel-shaped part 2, which free end serves for expelling liquid into a body cavity, such as rectum and up the intestinal duct.

Figure 3:
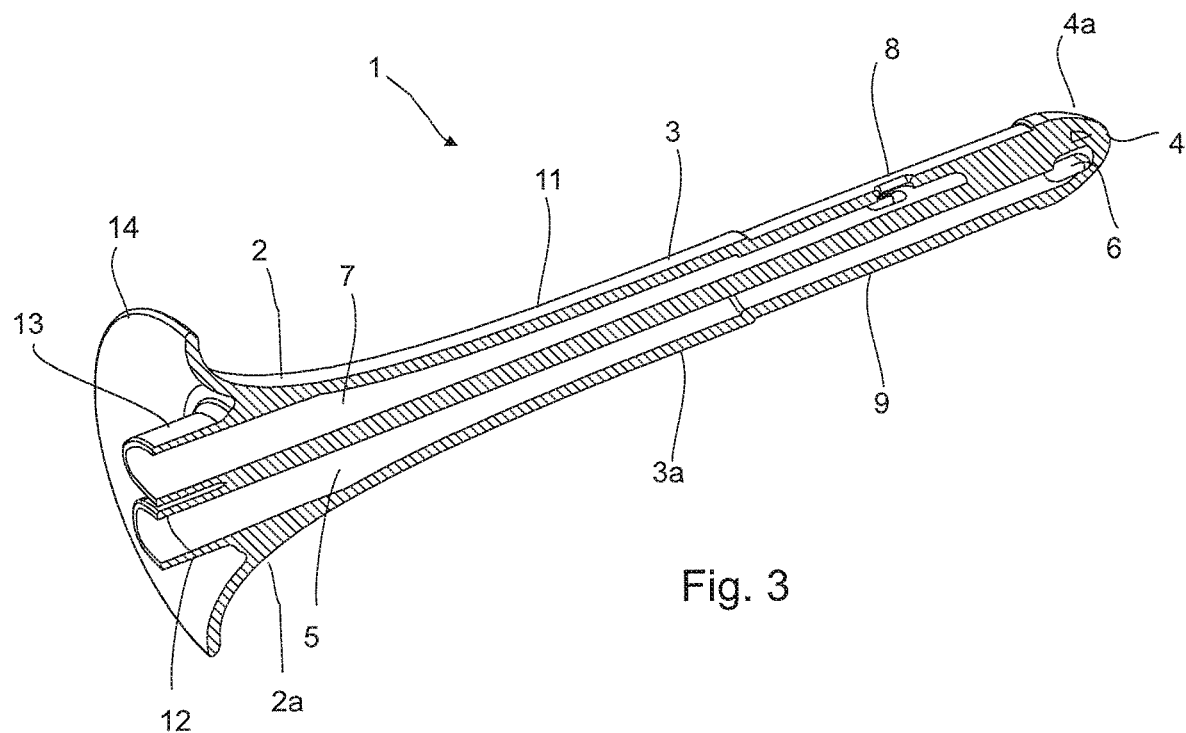
FIG. 3 is a longitudinal sectional view taken along line III-III in FIG. 1.
Figure 7:
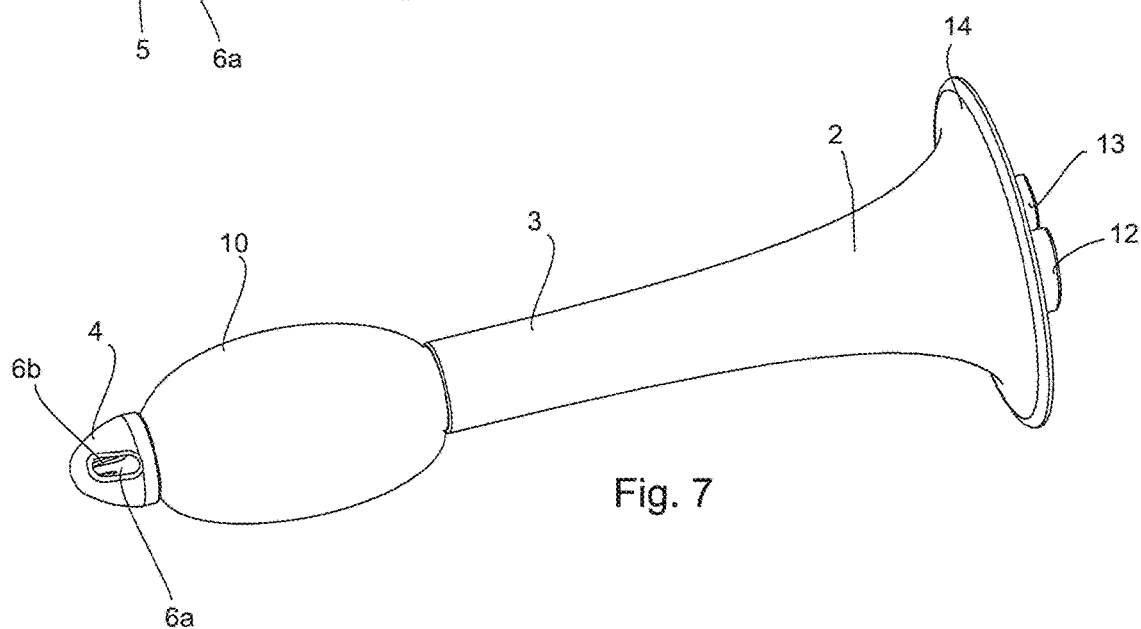
FIG. 7 shows the catheter provided with a fixation member in form of a balloon.

As seen more clearly in the longitudinal sectional view of FIG. 3 a liquid flow channel 5 extends lengthwise the funnel-shaped part 2 into the elongated catheter part 3 and ends in an injection opening 6 at the free end 4 of said elongated catheter part 3 to expel injection liquid flowing in a liquid flow channel 5 from an injection liquid reservoir (not shown). A fluid flow channel 7 extends parallel to the liquid flow channel 5 and is shorter than the liquid flow channel 5 to be able to expel a fluid, such as liquid, into a balloon 10, to expand the balloon 10 as illustrated in FIG. 7 to help keeping the catheter in a fixed position and substantially sealed against the wall of the body cavity during irrigation. To that aspect the fluid flow channel 7 ends in a delivery opening 8 at an elongate fixation section 9 of the elongated catheter part 3 distal to the free end 4, which elongate fixation section 9 is surrounded by the expandable balloon 10, as seen in FIG. 7, which balloon is secured fluid-tight to said elongate fixation section 9.

The liquid flow channel 5, the fluid flow channel 7, the funnel-shaped part 2, and the catheter part 3 together define an integral main body 11 of the rectal catheter 1. The main body 11 is annularly delimited by annular funnel wall 3a at the funnel-shaped part 3. The annular funnel wall 3a tapers into annular catheter wall 2a of the catheter part 3a that terminates into a rounded, free end with a rounded free end wall 4a. Several delivery openings 8, such as two, may be provided through the annular catheter wall 2a although just one is visible in FIG. 1. Similarly, several injection openings 6, such as two or three, may be provided through the rounded free end wall 4a. Thus, the present invention is not limited to just one delivery opening 5 and one injection opening 6. The size of said openings 6,8 may be just a few mm, such as e.g. 5 mm, but may vary within the limits defined above, so that a gentle pumping pressure suffice for injection of liquid into either the balloon 10, which is seen in FIG. 7, or out through the injection opening 6, in a manner that is comfortable for the user.

Opposite the injection opening 6 the liquid flow channel 5 has a first tube connection piece 12, and opposite the delivery opening 8 the fluid flow channel 7 has a second tube connection piece 13. These tube connection pieces 12,13 are of an elastic and/or flexible material selected to fluid-tight seal around an object inserted into said tube connection pieces 12,13. The elasticity and/or flexibility allow the tube connection pieces 12,13 to expand, stretch, adapt, and/or assume any appropriate shape that intimately mates fluid-tight around an inserted object.

When using multi-component injection molding for manufacturing the rectal catheter 1, the tube connection pieces 12,13 can be made in the same molding process as the main body 11, and thus when the rectal catheter 1 leaves the injection molding machine a rectal catheter 1 with flexible and/or elastic tube connection pieces 12,13 has been made in one and same manufacturing process.

The tube connection pieces 12,13 protrude axially and parallel beyond the flared portion 14 of the funnel-shaped part 2 to be easy accessible for coupling purposes. Since the tube connection pieces 12,13 are elastic and/or flexible they cannot only be stretched and retract to inherent memory-shape, they can also have bends to a certain extent. The length of the tube connection pieces 12,13 can vary within the scope of the present invention and may be shorter or longer than shown in the drawing. Accordingly, although it is preferred that the tube connection pieces 12,13 protrude beyond the flared portion 14 of the funnel-shaped part 2, this may not be mandatory for all embodiments.

Figure 1:
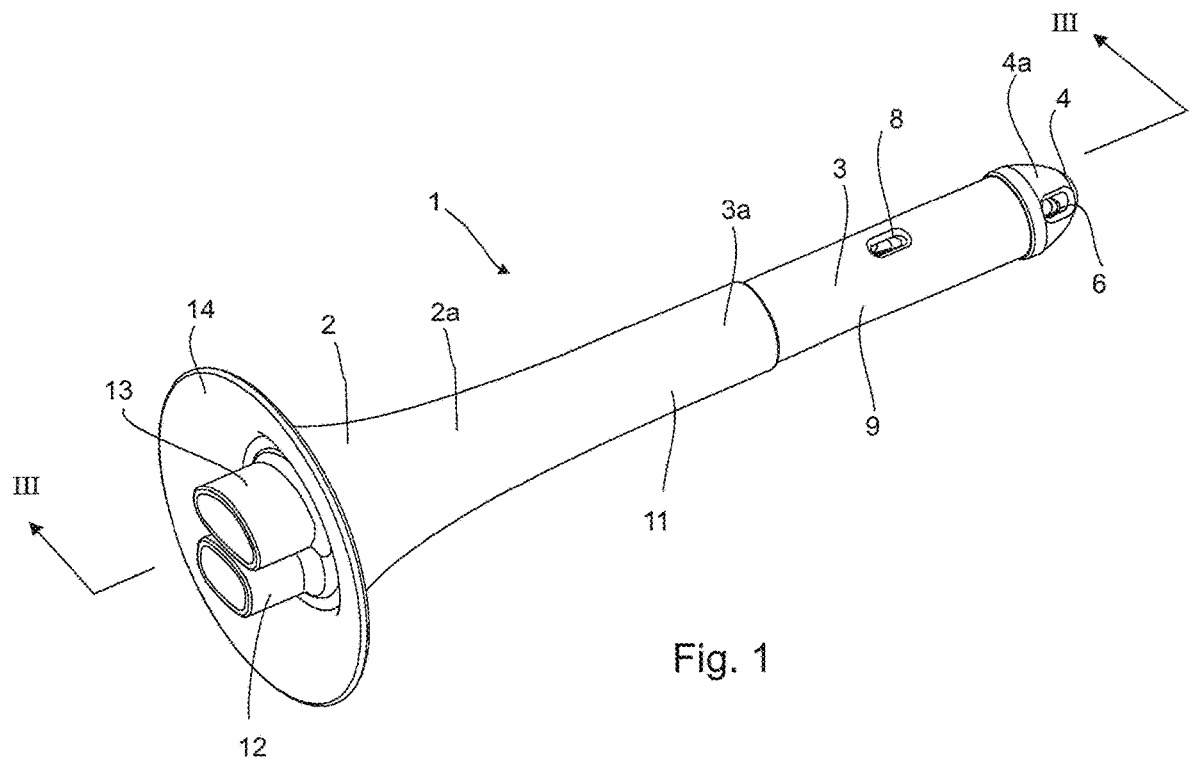
FIG. 1 is a perspective view of a first embodiment of a catheter without fixation member and seen from the funnel-shaped part.
Figure 2:
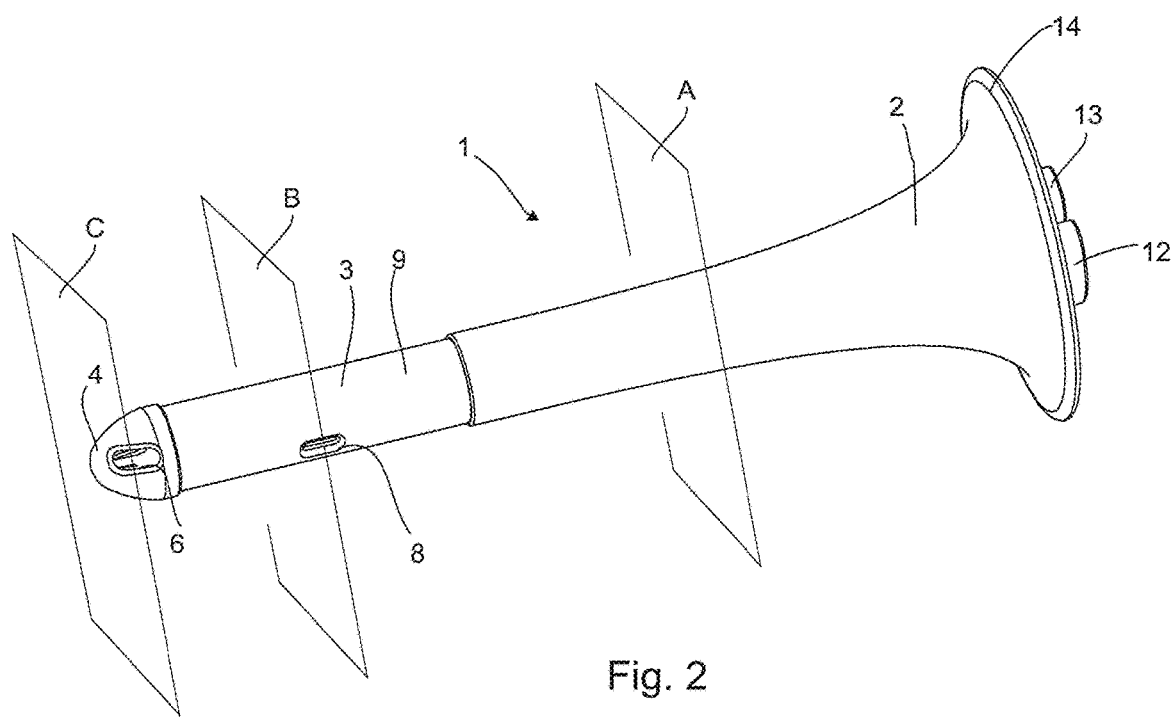
FIG. 2 shows the same seen from the free end of the catheter.

As seen best in FIG. 1, the cross-section of the first tube connection piece 12 is different from the cross-section of the second tube connection piece 13 to visualize and tactile-wise enabling identification of which tube connection piece 13 shall be used for expanding the balloon, and which tube connection piece 12 shall be used for expelling liquid out of the free end of the catheter part 3. The different cross-sections of the tube connection pieces 12,13 thus provide assembling guidance to the user. Moreover, the elastic and/or flexible properties of the tube connection pieces 12,13 make the catheter more user-friendly, more reliable to use with respect to obtaining fluid-tight connections to the tubes or hoses (not shown) for connecting to the injection liquid reservoir and/or fluid reservoir, which liquid reservoir and fluid reservoir may be the same or different. Since the elastic and/or flexible tube connection pieces 12,13 can be added to the main body 11 in the same multi-component injection molding process, manufacturing costs of these extra functionalities are low, which is reflected in the selling price. Different cross-sections of the connection pieces 12,13 are not mandatory, although preferred.

Figure 4:
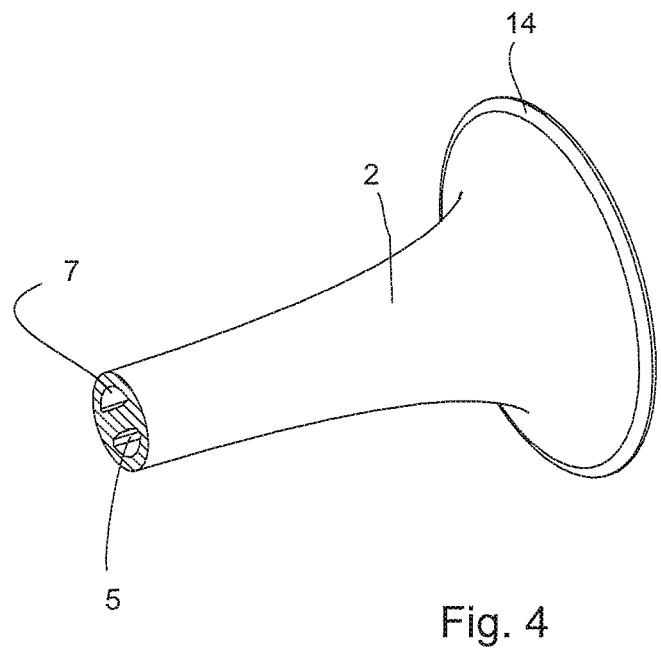
FIG. 4 is a cross-sectional view of the catheter part taken at plane A in FIG. 2.
Figure 5:
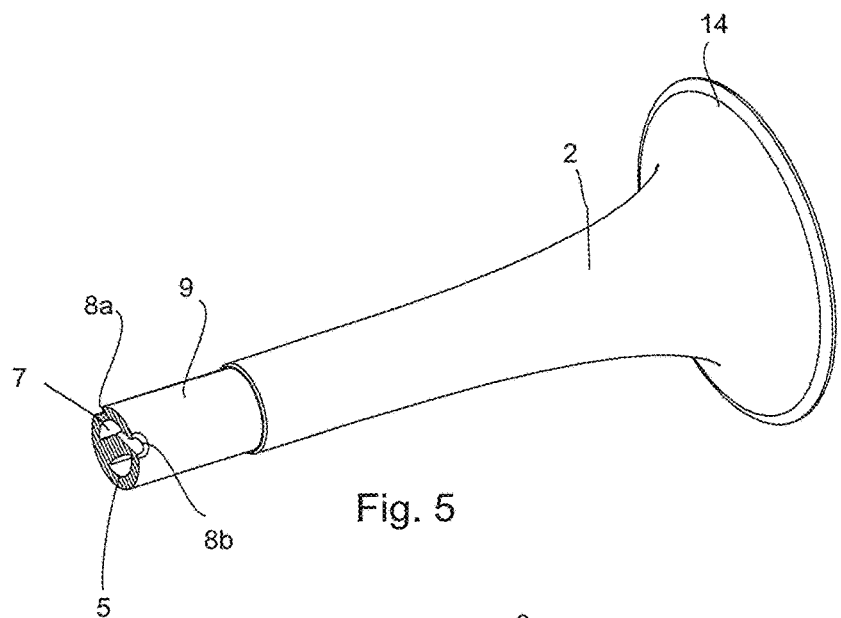
FIG. 5 is a cross-sectional view of the catheter part taken at plane B in FIG. 2.
Figure 6:
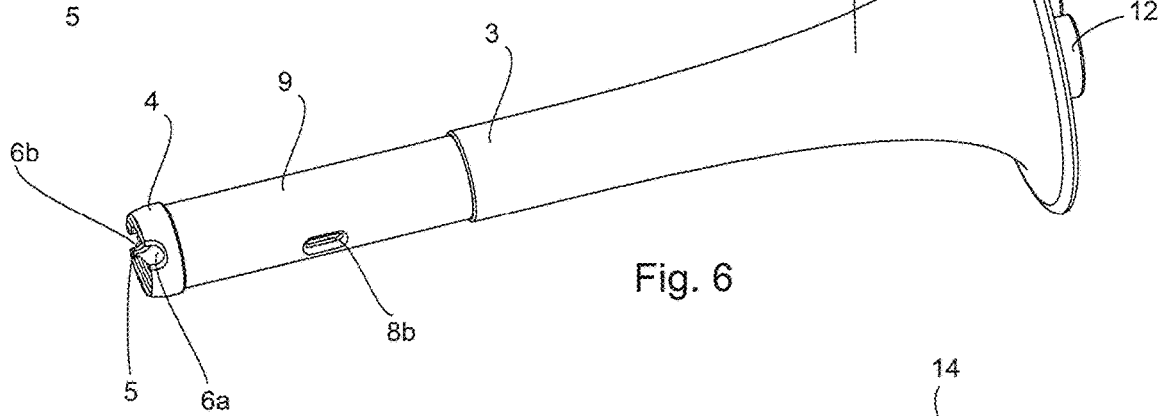
FIG. 6 is a cross-sectional view of the catheter part taken at plane C in FIG. 2.

Although the tube connection pieces 12,13 may have different cross-sections for user-friendliness, the same cross-section are not needed along the liquid flow channel 5 and the fluid flow channel 7, as can be seen in the cross-sectional view of FIGS. 4-6, where said cross-sections are shown as substantially of same size and cross-sectional shape.

FIG. 5 shows a cross-section of the elongate fixation section 9 of the catheter part 2 which is surrounded by the balloon 10. This section 9 has two opposite elongate delivery openings 8a,8b each of an area corresponding almost to the cross-sectional area of the fluid flow channel 7, at least in the catheter part 3. So the liquid flow out of the delivery openings 8a,8b is gentle and unobstructed without any negative throttling that increases expelling pressure to the discomfort of the user. A less dense fluid, such as air, can of course also exit the delivery opening unobstructed.

FIG. 6 shows a cross-section of the free end 4 of the catheter part 2. The free end 4 has two opposite elongate injection openings 6a,6b each of an area corresponding almost to the cross-sectional area of the liquid flow channel 5, at least in the catheter part 3. So the liquid flow out of the injection openings 6a,6b is also very gentle and unobstructed without any negative throttling that increases expelling pressure to the discomfort of the user.

Since the delivery openings 8a,8b and the injection openings 6a,6b are substantially larger than the small air holes provided in the prior art catheters for air as the sole expansion medium of the balloon, these delivery openings 8a,8b and injection openings 6a,6b can be made in the same injection molding process as the main body 11 and need not be made in a subsequent processing step. Thus the only subsequent processing step in order to make the first embodiment of a catheter of the present invention ready for use, is application of the balloon, and optionally provision of a surface coating, such as a hydrophilic surface coating.

Figure 8:
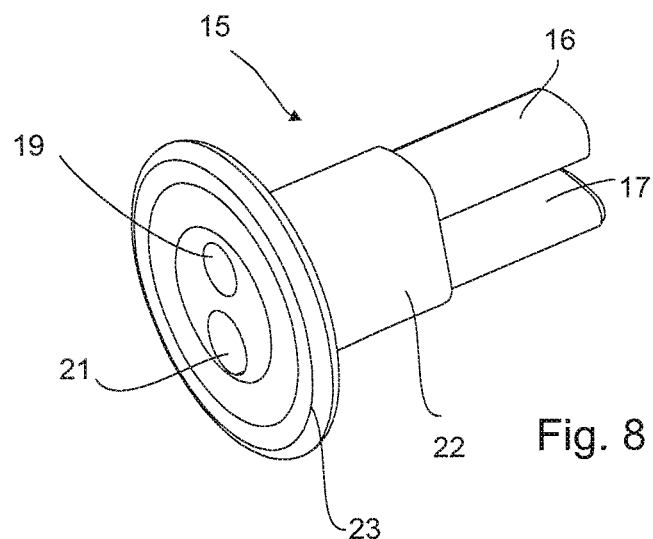
FIG. 8 shows a first embodiment of a coupling component in perspective seen from the tube connection part opposite the end for coupling to the catheter.
Figure 9:
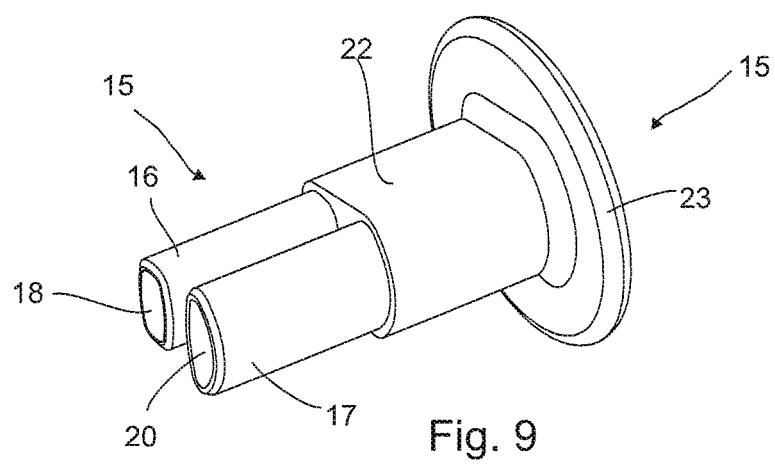
FIG. 9 shows the same seen from the end for coupling to the catheter.
Figure 10:
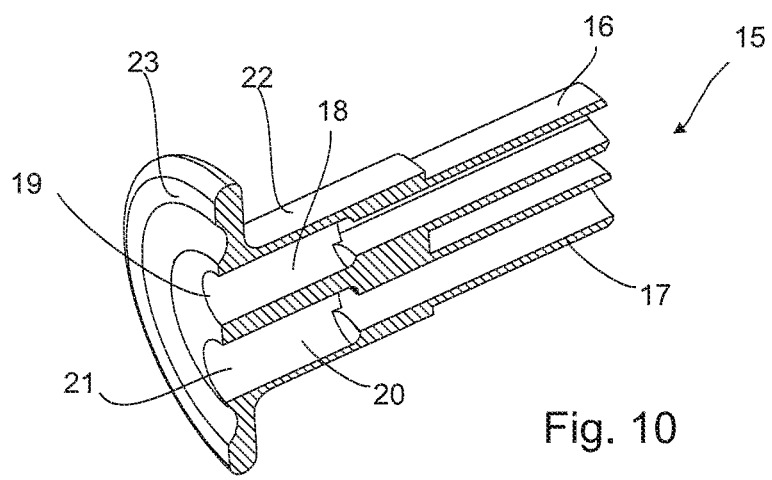
FIG. 10 is a longitudinal sectional view taken along line X-X in FIG. 8.

FIGS. 8 and 9 show a first embodiment of a coupling component 15 in two different perspective views. FIG. 10 is a longitudinal sectional view of FIG. 8 to illustrate the flow passages through said first embodiment of a coupling component 15.

The first embodiment of a coupling component 15 is e.g. used if the tubes or hoses (not shown) from the injection liquid reservoir (not shown) cannot be directly coupled to the rectal catheter, e.g. to allow the rectal catheter 1 to be used more universally, e.g. with tubes or hoses (not shown) from different manufacturers not necessarily immediate adapted for mating with the tube connections 12,13 of the rectal catheter 1 even though they 12,13 are elastic and/or flexible.

Preferably the catheter 1 may be supplied as a kit of parts also including pump means and valve means for controlling infusion of injection liquid and/or of expansion fluid. Optionally such a kit may also include a source of injection liquid in form of a liquid reservoir of e.g. saline or other of the above-mentioned liquids. The liquid for use in the present invention is not limited to water or saline but can include electrolyte solutions and medicament solutions delivered to the bowel for internal absorption and treatment, such as local treatment. Other exemplary liquids may include oils and/or laxatives. The injection liquid reservoir may be in the form of a plastic bag or a bottle, e.g. in form of a drip bag, and if air is used as the expansion fluid, the atmosphere may serve as the corresponding source of air.

The first embodiment of a coupling component 15 has a first flow connector 16 adapted to fluid-tight fit together with the first tube connection 12 piece and a second flow connector 17 adapted to fluid-tight fit together with the second tube connection piece 13.

A third straight flow channel 18 extends through the coupling component 15 from the first flow connector 16 to a first coupling opening 19 for coupling to a first tube or hose (not shown). A fourth straight flow channel 20 extends through the coupling component 15 from the second flow connector 17 to a second coupling opening 21 for coupling to a second tube or hose (not shown). The first embodiment of a coupling component 15 may have flow connectors 16,17, e.g. rigid flow connectors made of a thermoplastic material such as Nylon®, or a thermoset, to provide dimensionally stable flow connectors 16,17 to be introduced into the elastic tube connection pieces 12,13 of the rectal catheter 1. The opposite tube connecting part 22 of the coupling component 15 may optionally be elastic or flexible, e.g. to allow inserting conventional stepped tube connectors into the coupling openings 19,21. The tube connecting part 22 has a flange 23 to enforce the coupling openings and allow better grasping of the coupling component. The tube connecting part 22 need however not be elastic or flexible. A completely rigid coupling component is within the scope of the present invention. In case of an elastic and/or flexible tube connecting part 22 aligned with rigid flow connectors 16,17, the same multi-injection molding process as for the rectal catheter 1 can be used.

For the first embodiment of a coupling component 15 the third flow channel 18 and the fourth flow channel 21 are straight.

Figure 11:
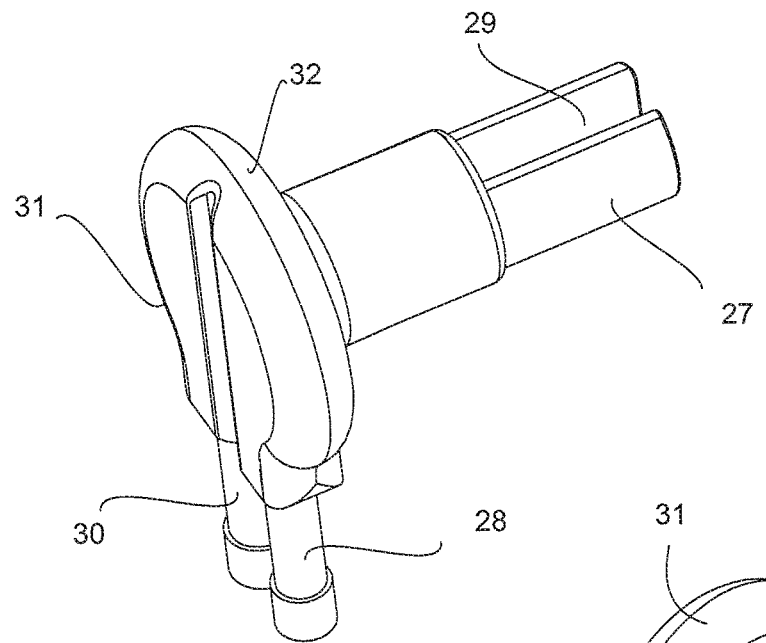
FIG. 11 shows a second embodiment of a coupling component in perspective seen from the tube connection part opposite the end for coupling to the catheter.
Figure 12:
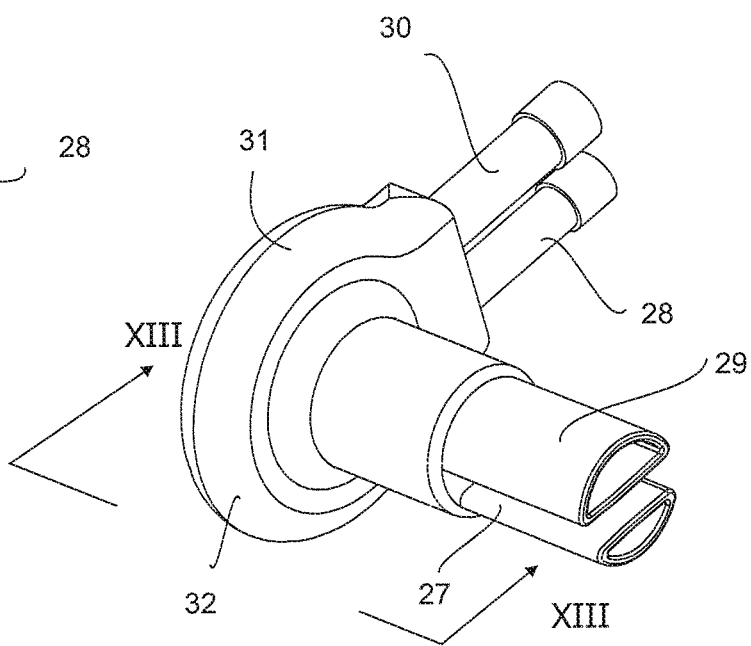
FIG. 12 shows the same seen from the end for coupling to the catheter.
Figure 13:
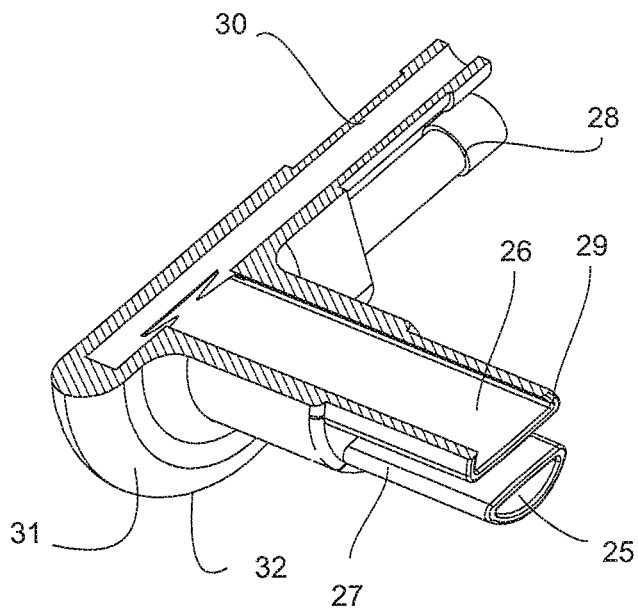
FIG. 13 is a longitudinal sectional view taken along line XIII-XIII in FIG. 11.

FIGS. 11-13 show a second embodiment of a coupling component 24 having a curved third flow channel 25 and a curved fourth flow channel 26. The third flow channel 25 runs in a first flow plane from a first flow connector 27 via a bending of about 90° into a first coupling piece 28. The fourth flow channel 26 runs from a second flow connector 29 via a bending of about 90° into a second coupling piece 30 in a second flow plane substantially parallel to the first flow plane. Thus the second embodiment of a coupling component 24 differs essentially from the first embodiment of a coupling component 15 in that it has coupling pieces 27,29 instead of coupling openings 19,21 for securing tubes or hoses for connecting to an injection liquid reservoir and/or an expansion medium reservoir, via respective pump means and valve means, and in having curved liquid flow channels 25,26 instead of straight. Although the curvature shown for the second embodiment of a coupling component 24 is illustrated to be a substantially right angle, other curvatures, such as smooth bends, larger angles above 90°, and even smaller angles below 90°, are within the scope of the present invention.

The curved configuration of the second embodiment of a coupling component 24 wherein the flow direction through the flow connectors 27,29 are different from the flow direction through the coupling pieces 27,29 is enabled by a flow converter member 31, inserted between the flow connectors 27,29 and the coupling pieces 28,30. The flow converter member 31 provides liquid communication between the flow connectors 27,29 and the coupling pieces 28,30 by providing the curved part of the respective third flow channel and fourth flow channel, while the part of the third flow channel and fourth flow channel through the respective flow connectors 27,29 and the coupling pieces 28,30 may be straight, as in the first embodiment of a coupling component 15.

The flow converter member 31 may have an enlargement 32 for improving the grasping facility of the second embodiment of a coupling component 24.

Also the first embodiment of a coupling component 15 can have elongate coupling pieces 28,30 instead of just coupling openings 19,21 in order to extend the third flow channel 18 and the fourth flow channel 20. The elongate coupling pieces 28,30 may be rigid or elastic as required for a given coupling task and coupling environment.

Furthermore, the coupling pieces 28,30 may be longer than shown, e.g. extend into flexible tubes that serve for connecting to a valve means.

Depending on the actual irrigation environment, the convenience around the user, the users preferred position during irrigation, and the further equipment, the user may choose to use any of the coupling components 15,24, or none at all together with the first embodiment of a catheter 1.

Figure 14:
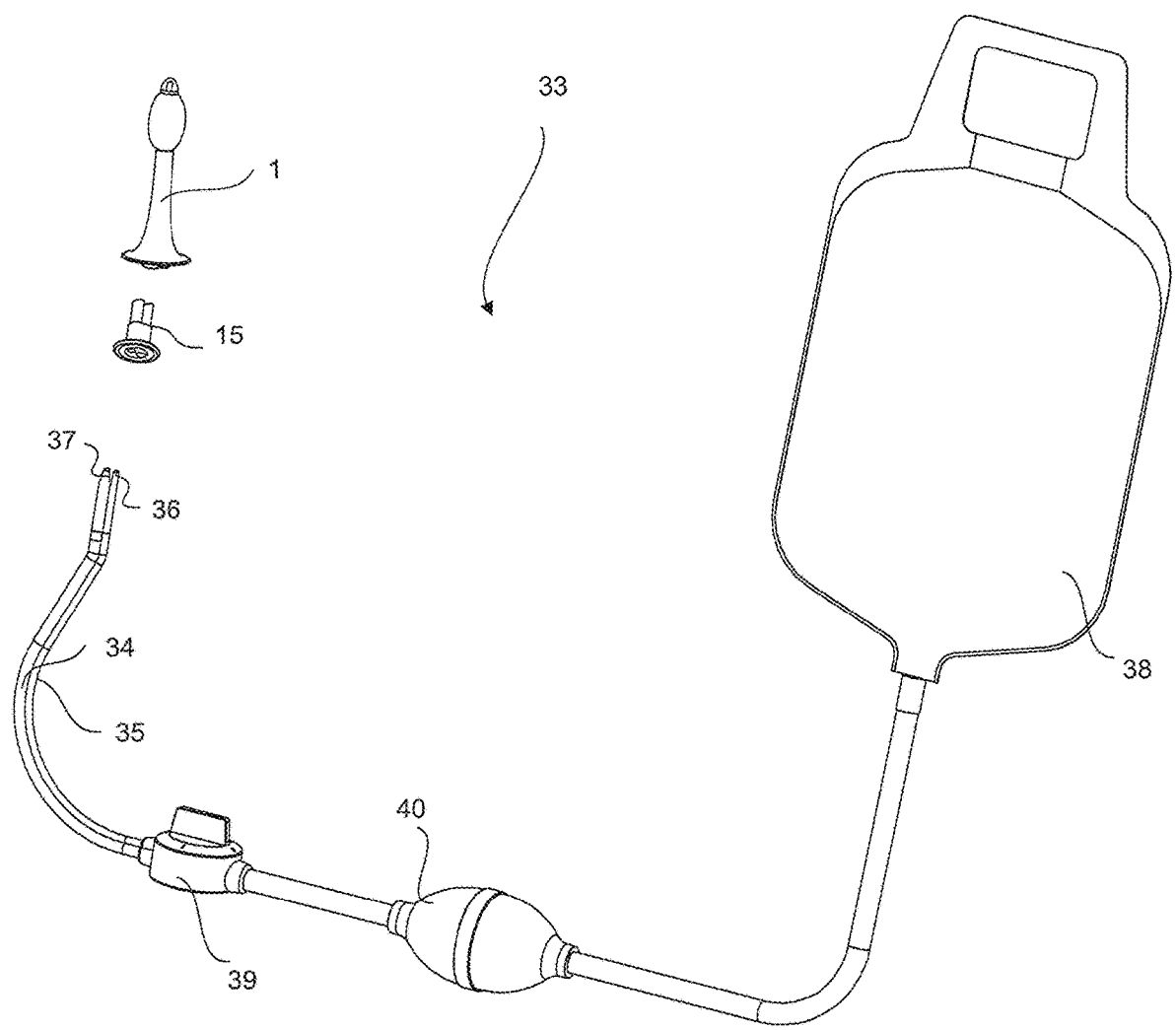
FIG. 14 shows a partially exploded view of an injection apparatus using the catheter and the coupling component.

FIG. 14 shows, in a partly exploded view, a rectal injection apparatus 33 using the rectal catheter 1 and in the situation where it is about to be connected to a liquid tube 34 and a fluid tube 35, which in the example also is a liquid tube, via the first embodiment of a coupling component 15, as described above. The tubes 33,34, which is embodied by a dual lumen tube, have, just as an example, tapered tube connectors 36,37 for inserting into the first coupling opening 19 and the second coupling opening 21, respectively. The tubes 33,34 are in liquid communication with an injection liquid reservoir 38 via a valve means 39 and a pump means 40, as e.g. described in applicant's patent application Ser. No. 10/747,405.8. The pump means 40 is of the kind adapted to switch between flow to the liquid flow channel 5 and to the fluid flow channel 7, and the pump means 40 can e.g. be a hand-operated rubber ball pump or inflator having an intake side in liquid communication with the injection liquid reservoir and an outlet side in liquid communication with the rectal catheter 1 via the pump means 40.

The coupling components 15,24 can be a separate component or a component prefixed to the catheter 1, e.g. by being made as an integral part of the catheter during the injection molding, or be attached and secured by gluing, or the coupling components 15,24 can be assembled with the catheter just prior to use.

Although the apparatus shown in FIG. 14 utilizes a first embodiment of a coupling component together with a first embodiment of a catheter, use of the second embodiment of a coupling component for said first embodiment of a catheter is also within the scope of the present invention. Similarly, the tube coupling adaptor can be used in an apparatus set up similar to the set up shown in FIG. 14 together with the second embodiment of a catheter, the tubes, valve means, and the injection liquid reservoir. The tubes may be separate tubes or a dual lumen tube.

Figure 15:
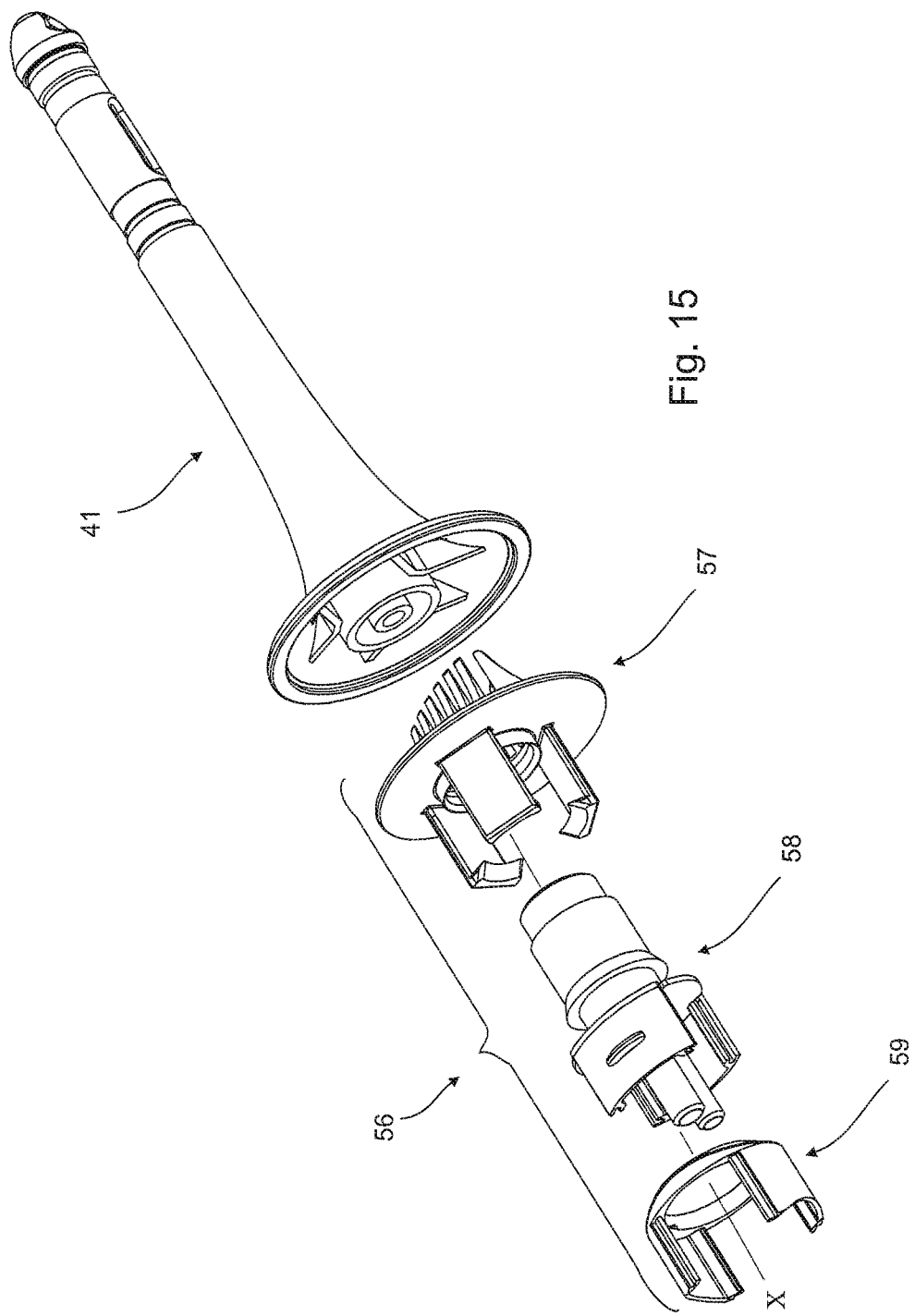
FIG. 15 shows an exploded perspective view of a second embodiment of a catheter shown for illustrative purposes without fixation member, and of the three sub-components: a catheter connector component, a third embodiment of a coupling component, and a decoupling component, of a tube coupling adaptor to be used with said second embodiment of a catheter.

FIG. 15 shows, in an exploded perspective view, a catheter assembly including a second embodiment of a catheter 41 of the present invention, which catheter 41 is shown without its fixation member 10. The second embodiment of a catheter 41 generally resembles the first embodiment of a catheter 1 and for like parts same terminology and reference numerals are used.

The second catheter embodiment 41 has a funnel-shaped part 42 that tapers into an elongated catheter part 43. The elongated catheter part 43 has a free end 44 opposite the funnel-shaped part 42, which free end 44 serves for expelling liquid into a body cavity.

Figure 17:
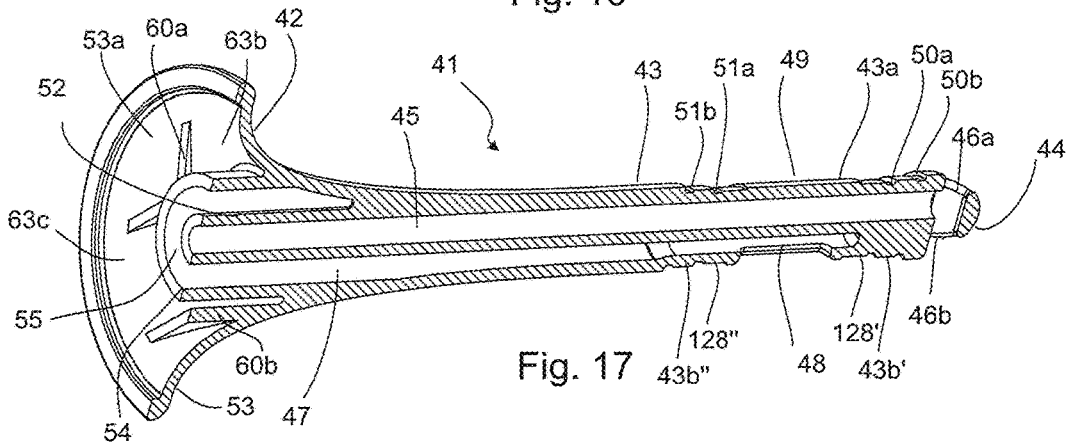
FIG. 17 is a longitudinal sectional view of the catheter seen in FIG. 16 taken along line XVII-XVII.

As seen more clearly in the longitudinal sectional view of FIG. 17 a liquid flow channel 45 extends lengthwise the funnel-shaped part 42 into the elongated catheter part 43 and ends in two opposite injection openings 46 at the free end 44 of said elongated catheter part 43 to expel injection liquid flowing in the liquid flow channel 45 from an injection liquid reservoir, e.g. the drip bag 38 seen in FIG. 14. A fluid flow channel 47 that surrounds the liquid flow channel 45 ends in an elongate delivery opening 48 at an elongate fixation section 49 of the elongated catheter part 43 distal to the free end 44. The elongate fixation section 49 is configured for attaching and fluid-tight securing the fixation member (not shown) so that said fixation member surrounds the elongate fixation section 49 above the delivery opening 48, similarly as described above for the first embodiment of a catheter 1, and below in relation to FIG. 28 of the second embodiment of a catheter 41. The number and shape of delivery opening(s) and injection opening(s) shown in relation to the second embodiment of a catheter 41 can vary within the scope of the present invention. Just one delivery opening or injection opening may suffice if sufficiently large.

The annular catheter wall 43a has one or more first annular recesses 50a,50b between the delivery opening 48 and injection openings 46a,46b, in the present embodiment two first annular recesses 50a,50b, and one or more second annular recesses 51a,5b distal to the delivery opening 48, thus between said delivery opening 48 and the funnel-shaped part 42. The purpose and structure of the annular recesses will be explained in further details in relation to FIG. 28.

Opposite the injection openings 46a,46b the liquid flow channel 45 ends inside the funnel-shaped part 42 in a first tube connection piece 52 that protrudes axially inside the flared portion 53 of the funnel-shaped part 42. The fluid flow channel 47 at least partly surrounds the liquid flow channel 45 at the flared portion 53 of the funnel-shaped part 42, and the second tube connection piece 54 surrounds the first tube connection piece 52.

The annular gap 55 between the first tube connection piece 52 and the second tube connection piece 54 provides for the part of the annular fluid flow channel 47 through the funnel-shaped part 42. The first tube connection piece 52 and the second tube connection piece 54 are in the present embodiment concentric and coaxial at least at the funnel-shaped part 42, and the annular fluid flow channel 47 may partly surround a length of the liquid flow channel 45 at least until the delivery opening 48. Accordingly, the annular fluid flow channel 47 extends into the elongated catheter part 43 as a parallel and/or partly annular liquid flow channel that ends at the delivery opening 48. The term "partly annular" serves to clarify the annular extent may be less than 360°. The remainder of the partly annular extent may be solid with the catheter wall. The first tube connection piece 52 and/or second tube connection piece 54 may be elastic, as described for the first embodiment of a catheter 1, to receive rigid, male fluid connectors. Such elastic tube connection pieces 52,54 may be provided to the catheter by 2K molding as described above for the first embodiment of a catheter 1.

The first tube connection piece 52 and the second tube connection piece 54 protrude substantially concentrically from the funnel-shaped part to be easy accessible for coupling together with a tube coupling adaptor 56, which tube coupling adaptor 56 includes a third embodiment of a coupling component in form of a tube connection component 58, as illustrated in the exploded view of FIG. 15.

Alternatively, the first tube connection piece 52 and the second tube connection piece 54 may protrude so that the first tube connection piece 52 is arranged eccentrically within the second tube connection piece 54.

As shown in FIG. 15 the tube coupling adaptor 56 consists of three sub-components: a catheter connector component 57, a tube connection component 58, and a decoupling component 59.

Figure 19:
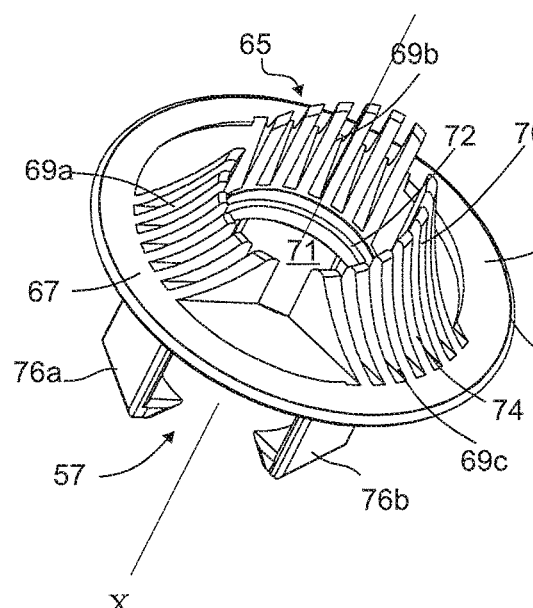
FIG. 19 is a perspective view of the catheter connector component from the catheter facing end.
Figure 20:
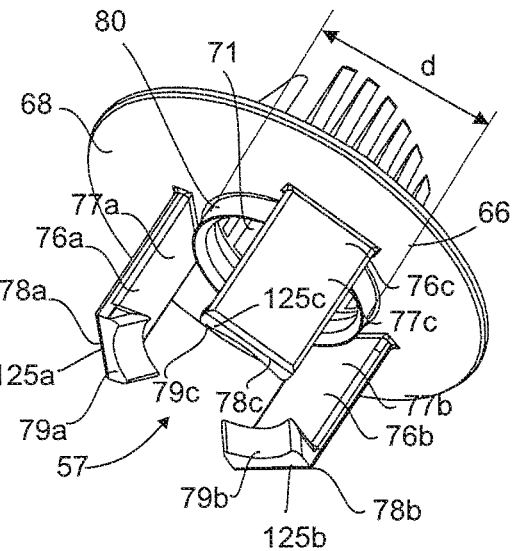
FIG. 20 shows the same seen from the opposite end.

The catheter connector component 57 of the tube coupling adaptor 56 is seen in enlarged scale perspective views in FIGS. 19 and 20. The catheter connector component 57 serves as an intermediate component for joining the tube connection component 58 and the funnel-shaped part 42 to create fluid communication between a liquid reservoir and the catheter 41 to supply liquid to the liquid flow channel 45 via the first tube connection piece 52 and fluid to the fluid flow channel 47 via the second tube connection piece 54.

Figure 16:
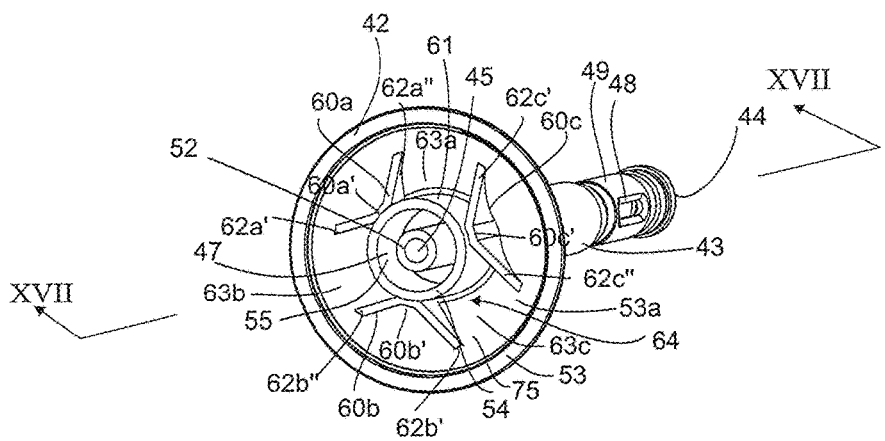
FIG. 16 shows the second embodiment of the catheter seen in FIG. 15 viewed in perspective from the funnel-shaped part.

As seen best in FIG. 16 the funnel-shaped part 42 has spaced apart partition webs 60a,60b,60c arranged around the second tube connection piece 54 to prevent the tube connection pieces 52,54 from yielding and bending too much when a male flow connector is to be attached, optionally to keep the second tube connection piece 54 apart from the first tube connection piece 52.

In the present exemplary embodiment three partition webs 60a,60b,60c are arranged equidistantly around the second tube connection piece 54, however more or less partition webs arranged at same or different distances are within the scope of the present invention provided that the tube coupling adaptor 56 is modified accordingly for proper coupling. Each partition web 60a,60b,60c is slightly V-shaped. The respective apices 60a',60b',60c' of the V-shaped partition webs 60a,60b,60c are united with the exterior annular wall 61 of the second tube connection piece 54, and the free legs 62a',62a"; 62b',62b"; 62c',62c" of the V-shaped partition webs 60a,60b,60c are united with the interior wall 53a of the flared portion 53 of the funnel-shaped part 42 to, in-between opposite sets of legs 62a",62c';62c",62b';62b", 62a' of opposite partition webs 60a,60b,60c, delimiting coupling gaps 63a,63b,63c. The partition web 60a,60b,60c, the first tube connection piece 52 and the second tube connection piece 54 define a second embodiment of a first coupling means 64 inside the flared portion 53 of the funnel-shaped part 42.

Figure 18:
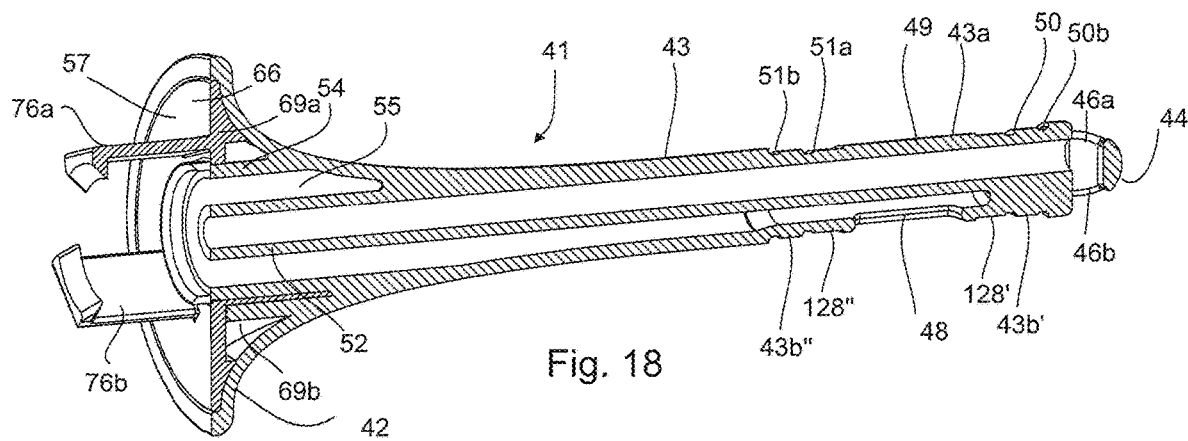
FIG. 18 shows the same but with the catheter connector component of the tube coupling adaptor secured to the funnel-shaped part of the catheter.

The first coupling means 64 serves for coupling with a second coupling means 65 on at least the catheter connector component 57 shown in different perspective views in FIGS. 19 and 20 to be fitted firmly inside the flared portion 53 of the funnel-shaped part 42, as seen in FIG. 18.

The catheter connector component 57 is composed of a ring-shaped collar 66 having a first collar face 67 and an opposite second collar face 68. Three groups 69a,69b,69c of finger webs 70 are circumferentially arranged axially jutting on the first collar face 67 to engage inside the coupling gaps 63a,63b,63c of the funnel-shaped part 42 to couple the catheter 41 and the catheter connector component 57 together. The ring-shaped collar 66 delimits a central collar opening 71 that receives the second tube connection piece 54 in fluid-tight engagement. Optionally an elastic sealing ring 72 may be provided along the collar opening 71 to optimize the sealing engagement between the second tube connection piece 54 of the catheter 41 and the collar opening 71 of the ring-shaped collar 66 of the catheter connector component 57.

A respective group 69a,69b,69c of jutting finger webs 70 is composed of a plurality of mutually spaced apart, but adjacent, flat finger webs 70 that are lowest towards the perimeter 73 of the ring-shaped collar 66 and highest at the collar opening 71. In the present embodiment of a catheter connector component 57 the height of the jutting finger webs 70 in a group 69a,69b,69c of such jutting finger webs 70 increases gradually from the perimeter 73 of the ring-shaped collar towards the collar opening 71 to a maximum height that allows said group 69a,69b,69c to be located fully inside the coupling gaps 63a,63b,63c of the funnel-shaped part 42. Preferably the height of the jutting finger webs 70 in a group 69a,69b,69c increases along a radially extending curvature corresponding to the curvature of the interior face of the flared portion 53 of the funnel-shaped part 42, so that the free curved edges 74 of the jutting finger webs 70 abut said interior face 75 of the interior wall 53a of the flared portion 53 of the funnel-shaped part 42 when the catheter connector component 57 are mounted in the flared portion 53, as shown in FIG. 18.

The ring-shaped collar 66 abuts, or substantially abuts, the flared portion 53 of the funnel-shaped part 42, so that the engagement of the first coupling means and the second coupling means is further supported and stabilized.

Due to the jutting finger webs 70 being arranged spaced apart with a small distance to each other in a group 69a, 69b,69c of jutting finger webs 70, the jutting finger webs 70 become circumferentially flexible in relation to each other, so that when such a group 69a,69b,69c of jutting finger webs 70 are pressed inside a respective coupling gap 63a,63b,63c the jutting finger webs 70 are pressed together so that a clamping force is exerted on the V-shaped partition webs 60a,60b,60c, thereby firmly and resiliently coupling the catheter connector component 57 together with the catheter 41.

The catheter connector component 57 can be mounted to the catheter 41 at any appropriate and convenient time, but most people prefer to mount the catheter connector component 57 or the combined tube coupling adaptor 56 with attached tubes 34,35 in advance of use of the catheter 41, e.g. before the catheter 41 is inserted into rectum.

Three flexible first clamping legs 76a,76b,76c protrude axially and circumferential spaced apart from the second collar face 68 and is configured for coupling with the tube connection component 58 seen in FIGS. 23-25.

A flexible first clamping leg 76a,76b,76c is substantially L-shaped with a respective axially extending leg 77a,77b, 77c secured to and protruding from the second collar face 68 towards a respective free end 78a,78b,78c that has a respective radially extending leg 79a,79b,79c bending towards the central axis X of the catheter connector component 57. The radially extending leg 79a,79b,79c constitutes the foot of the L-shaped flexible first clamping leg 76a,76b,76c. The dimensions of the flexible first clamping legs 76a,76b,76c, in particular the length of the axially extending leg 77a,77b, 77c and of the radially extending leg 79a,79b,79c, are selected to clamp firmly together with the tube connection component 58.

Because the first tube connection piece 52 is arranged inside the second tube connection piece 54 neither the first embodiment of a coupling piece 15 nor the second embodiment of a coupling piece 24 can be used with the second embodiment of the catheter 41. Instead the tube coupling adaptor 56 is inserted between the tubes 34,35 and the catheter 41. The tube coupling adaptor 56 is configured to divert liquid flowing in parallel tubes 34,35 into tube connection pieces 52,54 and flow channels that are arranged in surrounding relationship.

The flexible first clamping legs 76a,76b,76c of the tube connection component 58 are arranged annularly around, and radially spaced apart from, a tubular third coupling piece 80 provided along the perimeter of the collar opening 71, which tubular third coupling piece 80 guides and receives the free end of a tubular front end part 81 of the tube connection component 58 when the tube coupling adaptor 56 are secured on the catheter 41.

Rather than the first tube 34 and the second tube 35 being arranged one surrounding the other, such tubes are normally arranged side by side. As shown in FIGS. 23-25 the third embodiment of a coupling component 56 of the tube coupling adaptor 56 is a tube connection component 58 that has the tubular front end part 81 for coupling to both the catheter 41 and to the catheter connector component 57. The tubular front end part 81 extends axially into an opposite tube connecting end part 82 that is configured to put the annular arrangement of the first tube connection piece 52 inside the second fluid connection piece 54 in liquid communication with the not-annularly arranged respective first tube 34 associated with the injection liquid reservoir and in fluid communication with the second tube 35 associated with the expansion fluid reservoir 38, which reservoirs in the present exemplary embodiment both are associated with the injection liquid reservoir.

The tubular front end part 81 has an axially extending third connection piece 83 for coupling to the annular arrangement of the first tube connection piece 52 and the second tube connection piece 54.

The third connection piece 83 of the tubular front end part 81 consists of an exterior tubular coupling piece 84 that surrounds an interior tubular coupling piece 85 to define a flow gap 86 in-between said coupling pieces 84,85. The radial distance R1 between the interior face 87 of the interior tubular coupling piece 85 and the exterior face 88 of exterior tubular coupling piece 84 defines a "wall thickness" of an combined annular wall 88 of the third connection piece 83, said wall thickness is defined by the combined wall thickness of said tubular coupling pieces 84,85 and the radial width of the flow gap 86, and said wall thickness is selected to fit sealingly inside the annular gap 55 between the first tube connection piece 52 and the second tube connection piece 54. When the third connection piece 83 is coupled to the catheter 41 the third connection piece 83 overlaps the tube connection pieces 52,54 lengthwise. Furthermore, the exterior diameter D1 of the third connection piece 83 may be substantially the same as the interior diameter d of the tubular third coupling piece 80 to guide the tubular front end part 81 into fluid-tight engagement with the first tube connection piece 52 and the second tube connection piece 54 of the funnel-shaped part 52 of the catheter 41, as shown in the fragmentary, sectional view of FIG. 27.

The exterior tubular coupling piece 84 of the third connection piece 83 of the tubular front end part 81 extends axially into a first exterior tubular section 89 that has a larger exterior diameter D2 than the exterior diameter D1 of the third connection piece 83, whereby a first annular exterior abutment face 90, a breast, is defined at an exterior transition 91 between the third connection piece 83 and the first exterior tubular section 89. The first annular exterior abutment face 90 abuts the free end of the second tube connection piece 54 in the state where the tube coupling adaptor 56 is secured to the catheter 41.

Similarly, the interior tubular coupling piece 85 extends via an interior transition 92 into an interior tubular section 92a with a reduced interior diameter D3 in relation to the interior diameter D1 of the interior tubular coupling piece 85 whereby an annular interior abutment face 93, a breast, is defined internally between the third connection piece 83 and the interior tubular section 92.

Figure 27:
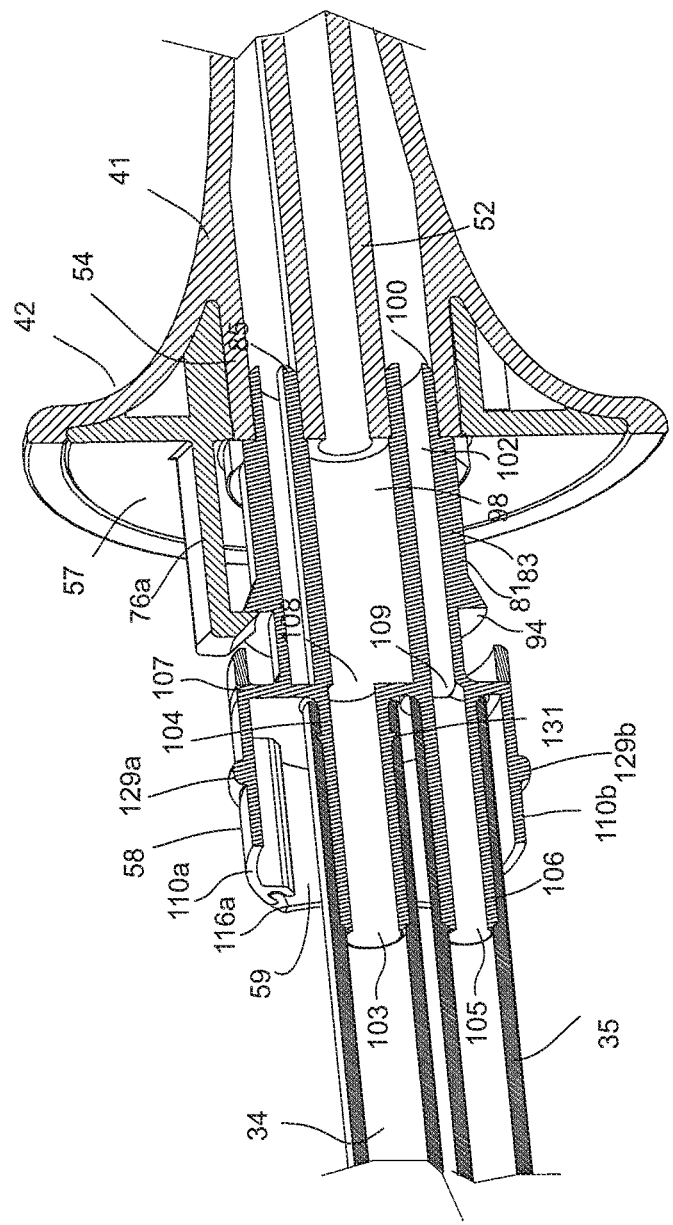
FIG. 27 is an enlarged sectional view of a central fragment of FIG. 26 where the tube coupling adaptor and the catheter are joined to engage.

The respective transitions 91,92 and abutment faces 90,93 provide a fluid-tight seal around the third connection piece 83 when said third connection piece 83 is inserted in the annular gap 55 between the first tube connection piece 52 and the second tube connection piece 54, e.g. by forcefitting, as illustrated in FIG. 27.

Axially opposite the first annular exterior abutment face 90 the exterior tubular section 89 has a coupling flange 94 that exposes a second annular exterior abutment face 95 to be grasped by the flexible first clamping legs 76a,76b,76c of the tube connection component 58, as also illustrated in FIG. 27. The coupling flange 94 has a largest diameter D5 that is larger than the exterior diameter D2 of the exterior tubular section 89. The axial length between the first annular exterior abutment face 90 and the second annular exterior abutment face 95 is selected in view of the length of the axially extending legs 77a,77b,77c of the catheter connector component 57 so that the radially extending legs 79a,79b, 79c of said catheter connector component 57 can releasably engage and hold together with the coupling flange 94.

The first exterior tubular section 89 extends axially into a second exterior tubular section 96 having an exterior diameter D6, that may be substantially equal to the exterior diameter D1 of the exterior tubular coupling piece 84, or at least smaller than the diameter D5 of the coupling flange 94, to provide an axial space for accommodating the radially extending legs 79a,79b,79c of the catheter connector component 57.

The interior tubular section 92a extends axially inside both the first exterior tubular section 89 and the second exterior tubular section 96, preferably concentrically.

The interior tubular coupling piece 85 and the interior tubular section 92a constitute a first flow connector 97 that delimits a first flow section 98 of a third flow channel 99. The exterior tubular coupling piece 84, the first exterior tubular section 89, the coupling flange 94, and the second exterior tubular section 96, that constitute a fluid flow connector 100, delimit the flow gap 86 as a first flow section 101 of a fourth flow channel 102 around the interior tubular coupling piece 85 and the interior tubular section 92. The tubular front end part 81 is preferably symmetrical along the longitudinal axis Y.

The first flow section 98 of the third flow channel 99 extends axially into a second flow section 103 of the third flow channel 99 inside a first coupling piece 104 for coupling to the first tube 34.

Similarly, the first flow section 101 of the fourth flow channel 102 extends axially into a second flow section 105 of the fourth flow channel 102 inside a second coupling piece 106 for coupling to the second tube 35.

A guide plate member 107 of the tube connecting end part 82 connects the second exterior tubular section 96 to the tube connecting end part 82 and serves to provide liquid communication between the first flow section 98 and the second flow section 103 of the third flow channel 99, and to provide fluid communication between the first flow section 101 and the second flow section 105 of the fourth flow channel 102.

In order to redirect the liquid flow through the first coupling piece 104 and the fluid flow through the second coupling piece 106, respectively, thus through the respective annularly arranged first flow sections 98,101 into the respective parallel second flow sections 100,105, or vice versa, the guide member 107 has a first aperture 108 coaxial with a second aperture 109. The second aperture is located to only allow fluid to flow through the fourth flow channel 102, and the first aperture 108 is located to only allow liquid to flow through the third flow channel 99.

To achieve this required control of the liquid flow and fluid flow from the tubes 34,35 into the catheter 41 and the fixation member 10, respectively, the guide plate member 107 of the tube connecting end part 82 of the third embodiment of a coupling component 58 covers the annular flow gap 86 except at the second aperture 109 to thereby directing fluid, preferably injection liquid into the second section 105 of the fourth flow channel 102 of the second coupling piece 106.

In the embodiment of the third coupling component 58 the first aperture 108 is eccentric to the first section 98 of the third flow channel 99 whereby the internal diameter D3 of the first section 98 only partly overlaps said first aperture 108. However, in a modified embodiment the third embodiment 58 of a coupling component the coupling pieces 104,106 may be arranged at a distance from each other that allows the first aperture 108 to be coaxial with the first section 98 of the third flow channel 99.

Two opposite flexible second clamping legs 110a,110b extend lengthwise adjacent the first coupling piece 104 and the second coupling piece 106 exterior to said coupling pieces 104,106. Each of the first flexible second clamping leg 110a and the second flexible clamping leg 110b has a lengthwise extending first free edge 111 and an opposite lengthwise extending second free edge 112. The first free edge 111 has a first female coupling profile 113 and the second free edge 112 has a second female coupling profile 114, which female coupling profiles 113,114 in the present embodiment of a tube connection component 58 are similar.

Figure 21:
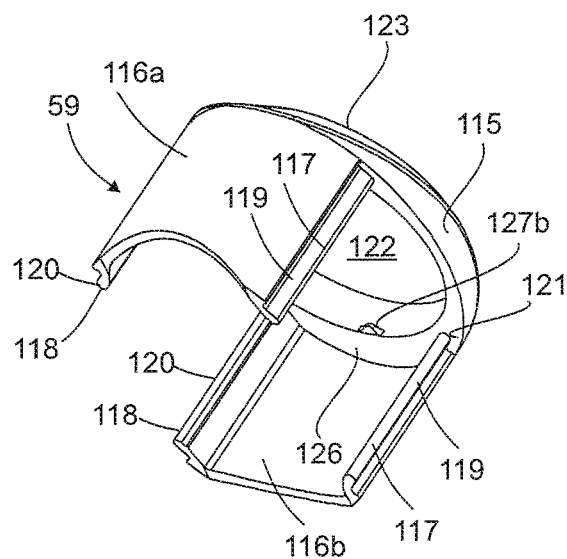
FIGS. 21 and 22 are different perspective views of the decoupling component for disengaging the catheter connector component that is engaging the tube connection component seen in FIGS. 23-25.
Figure 22:
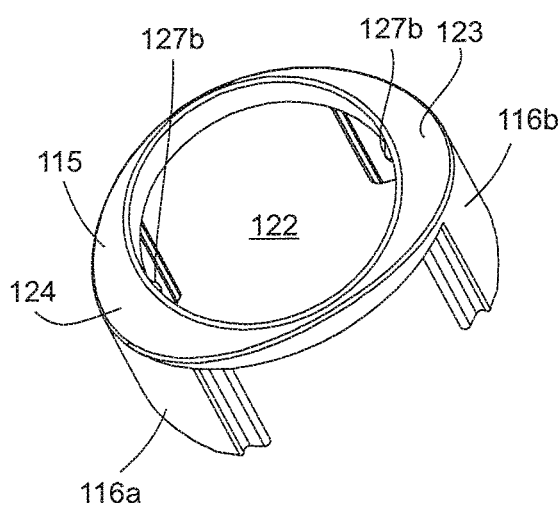
Figure 26:
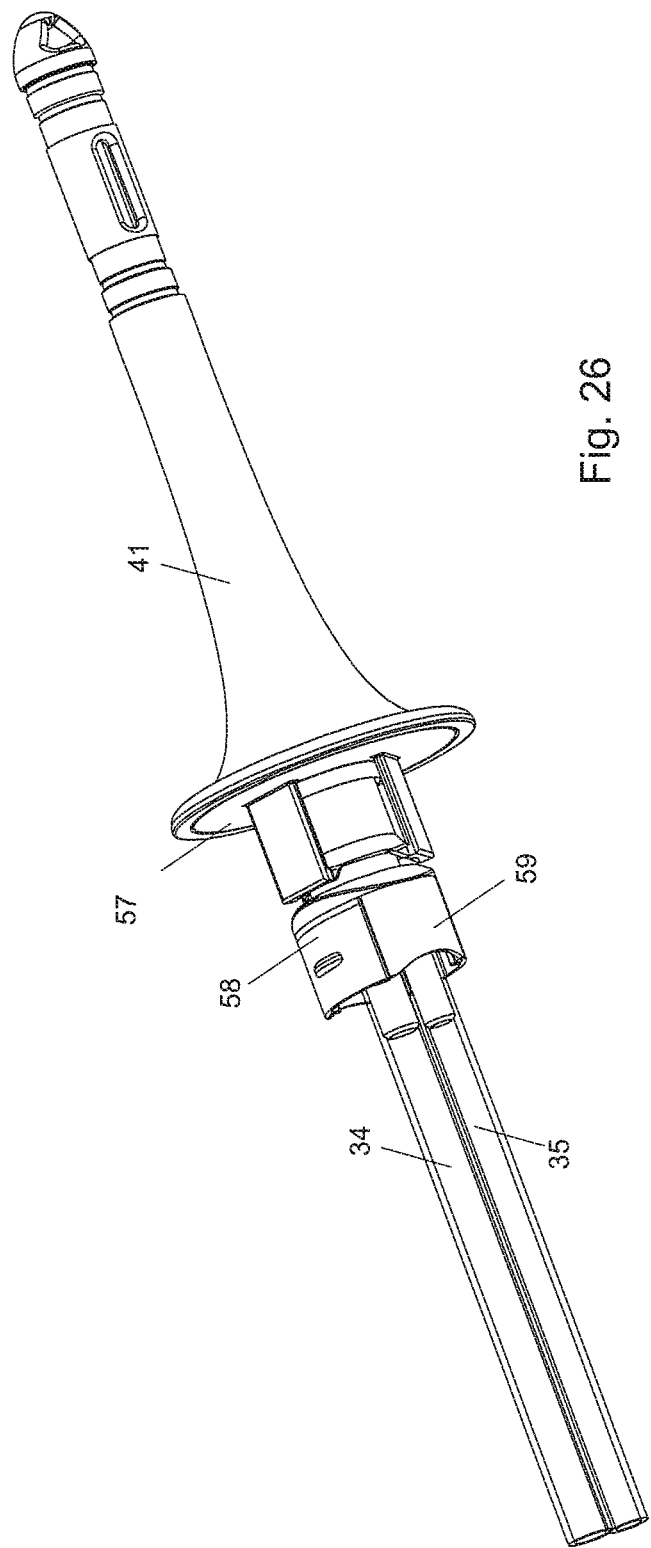
FIG. 26 shows the second embodiment of a catheter provided with the tube coupling adaptor to which tubes are connected for establishing fluid communication to an injection liquid reservoir, as e.g. shown in FIG. 14.

The decoupling component 59 seen in FIGS. 21 and 22 is composed of a ring-shaped release body 115. Two lengthwise extending releaser legs 116a,116b protrude from an exterior perimeter 121 of the ring-shaped release body 115. Each releaser leg 116a,116b has a first slide edge 117 and an opposite second slide edge 118. The first slide edge 117 has a first male coupling profile 119 and the second slide edge has a second male coupling profile 120.

The releaser legs 116a,116b of the decoupling component 59 fit between the flexible second clamping legs 110a,110b so that the male coupling profiles 119,120 slidingly can engage the female coupling profiles 113,114 to allow the decoupling component 59 to be displaced towards the catheter connector component 57 to actuate disengagement of the tube connection component 58 and the catheter connector component 57.

It should be noted that other arrangements of decoupling component and coupling profiles are within the scope of the present invention. For example, in an alternative embodiment a female coupling profile 113,114 can be provided on the decoupling component 59 and a male coupling profile 119,120 be provided on the tube connecting end part 82 of the tube connection component 58. In yet an alternative embodiment of a decoupling component a releaser leg 116a,116b or flexible second clamping legs 110a,110b can have both a male coupling profile and a female coupling profile.

The ring-shaped release body 115 has a circumferentially outwards tapering end wall 123 that delimits a release body opening 122. The circumferential tapering end wall 123 has a circumferential inclined release face 124, which, when the decoupling component 59 is moved towards the radially extending legs 79a,79b,79c of the tube connection component 58, applies a force on respective tapering free inclined edges 125a,125b,125c of the radially extending legs 79a, 79b,79c to spread apart said radially extending legs 79a, 79b,79c, whereby the tube connection component 58 is released from the catheter connector component 57. Any structure that can trigger disengagement of the tube connection component 58 and/or the catheter connector component 57, e.g. by application of a radial force, are also within the scope of the present invention.

The radial wall thickness of the tapering end wall 123 at the releaser legs 116a,116b may be greater than between the releaser legs 116a,116b so that the exterior geometry of the circumferential tapering end wall 123 are substantially oval. The oval design helps the user to grasp on the decoupling component 59 and operate it even though the tube coupling adaptor 56 is out of sight. The oval design also confers an inherent guidance to the user to locate the decoupling component 59 to slide it towards the catheter 41 to release the catheter 41.

The guide plate member 107 may initially abut the interior face 126 of the ring-shaped release body 115, as seen in FIG. 27, in which position the flexible first clamping legs 76a,76b,76c and the flexible second clamping legs 110a, 110b have free ends in substantially same plane. Different length of the flexible first clamping legs 76a,76b,76c and the flexible second clamping legs 110a,110b may however arrange the respective free ends in different planes. Two opposite beads 127a,127b protrude from the perimeter of the release body opening 122 inside said opening to serve as tactile stops during e.g. a lengthwise axial reciprocation of the decoupling component 57.

Each of the flexible second clamping legs 110a,110b has a knob 129a,129b for better holding on to the tube connection component 58, e.g. when the tubes 34,35 are pressed around the first coupling piece 104 and the second coupling piece 106, respectively. The knobs also allows the user to clearly, both visually and tactile, to distinguish between the decoupling component 57 and the tube connection component 58 so that the decoupling component 57 is not operated accidentally during an enema.

In embodiments wherein the balloon is to be attached to the catheter by gluing glue can be applied to the respective elongate gluing sections 43b',43b" of the annular catheter wall 43a between the respective opposite first annular recesses 50a,51a and opposite second annular recesses 51b, 51b for adhering the fixation member 10, the balloon 10, to the catheter 41. The second annular recesses 51b,51b are the recesses farthest away from the elongate fixation section 49 and the first annular recesses 50a,51a are closest to the elongate fixation section 49.

Figure 28:
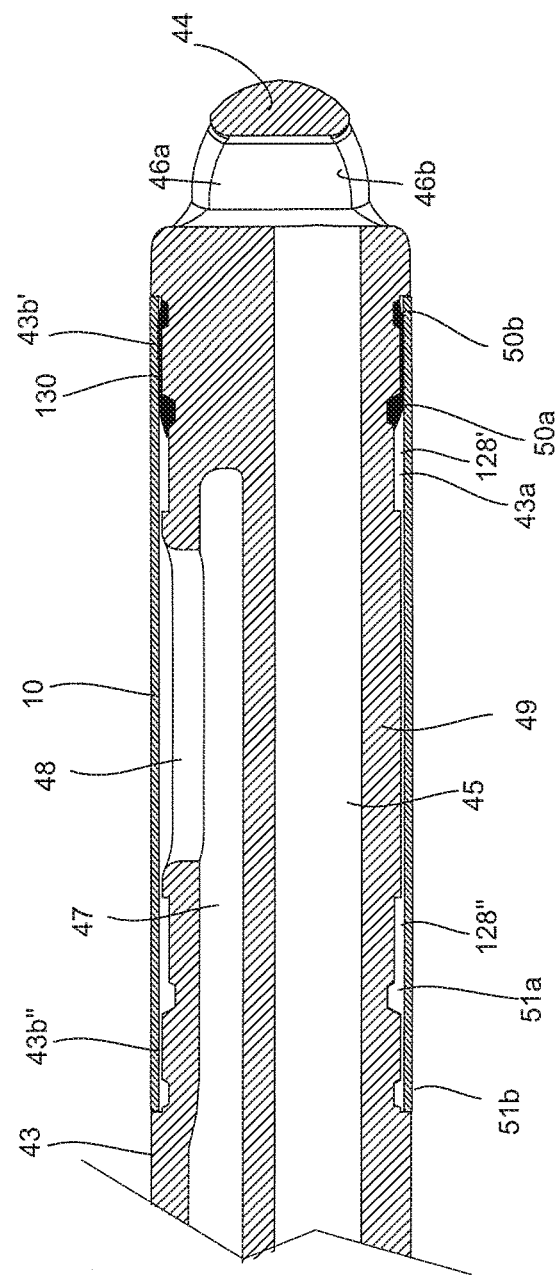
FIG. 28 is a sectional view of the catheter seen in FIG. 15, now provided with a not infused fixation member in form of a flat balloon.

As exemplified to the right in FIG. 28 the annular recesses 50a,50b;51a,51b can serve for receiving surplus of glue applied to the respective elongate gluing sections 43b',43b" so that the central part of the balloon does not unintentionally stick to the catheter, that glue does not enter the fluid flow channel and more or less blocks it, and that glue does not get into the delivery opening 48. The annular recesses 50a,50b;51a,51b allows for a sufficient large amount of glue to be applied to the respective elongate gluing sections 43b',43b" so that correct, firm and fluid-tight positioning and securing of the balloon 10 can be obtained without affecting the balloon's ability to be infused and distended later.

As illustrated to the left in FIG. 28, where no glue is added yet, to further prevent glue from harming the functionality of the balloon and the catheter the opposite first annular recesses 50a,51a also can have a respective run-off area 128',128" as an extra reservoir for any surplus of glue. When a contact pressure is applied to the balloon wall on top of the glue to make the balloon 10 adhere to at least the elongate gluing sections 43b',43b" any surplus of glue 130 can flow into the recesses, including into the run-off area 128',128" if needed. Emphasis is made that when the balloon is secured to the catheter by gluing both elongate gluing sections 43b',43b" are glued, and as a consequence one or more of the respective opposite first annular recesses 50a,51a and opposite second annular recesses 51b,51b take up glue. Thus, that the recesses 51a,51b to the left in FIG. 28 are free of glue is only for illustrative purposes to clearly show the design of the recesses.

Although the annular recesses 50a,50b;51a,51b are shown to have a slight V-shaped cross-section other cross-sections such as right-angled or U-shaped are also possible within the scope of the present invention. The depth and width of the annular recesses 50a,50b;51a,51b are adjusted and selected to accommodate glue in an amount to avoid that surplus glue makes the balloon stick to the catheter where is should not, and to avoid obstruction of flow channels and openings.

In order to improve the sealingly attachment of the tubes 34,35 to the respective coupling pieces 104,106, one or both of said coupling pieces may have one or more circumferentially protruding barbs of a continuous annular enlargement 131 that grasp on to the interior wall of the tubes 34,35. In the present embodiment of a tube connection component 58 only the first coupling piece 104 has a continuous annular enlargement 131 to indicate as guidance to the user which tubes must be connected to which coupling pieces.

The catheters of the present invention can be used either by the user himself/herself or with assistance. They can be used routinely, such as every day or every other day, and be disposable or reusable. A rectal catheter of the present invention can be used in an anal irrigation system as an alternative to other bowel management methods.

When a user operates a rectal catheter according to the present invention to irrigate the bowel, the fixation and irrigation can hardly be felt by the user due to the rather large injection opening(s) and delivery opening(s) that allow using liquid to fast expand the balloon to obtain sealingly fixation of the rectal catheter inside the rectum in order to prevent backflow when liquid subsequently is expelled out of the catheter part and into the bowel.

What is claimed is:

1. An assembly comprising a catheter and a coupling component, which catheter is adapted for injection of a liquid into a body cavity, said catheter being coupled to the coupling component adapted to couple to tubes for establishing fluid communication to an injection liquid reservoir, said catheter has
   a main body comprising a funnel-shaped part delimited by an annular funnel wall and an elongate tubular catheter part delimited by an annular catheter wall, which funnel-shaped part has a flared part that, via a smooth transition, tapers into a tapering part, which extend into the elongate tubular catheter part,
   the main body accommodates a liquid flow channel, which is adapted to expel the liquid via at least one injection opening in a free end of the elongate tubular catheter part opposite the funnel-shaped part, and
   an expandable fixation member that surrounds an elongate fixation section of the elongate tubular catheter part a distance from the free end of said elongate tubular catheter part, and a fluid flow channel which is adapted to, via at least one delivery opening provided in the elongate fixation section of the elongate tubular catheter part, deliver a fluid to the expandable fixation member,
   wherein the assembly comprises a tube coupling adaptor, the coupling component is a tube connection component being part of the tube coupling adaptor, and which tube coupling adaptor further comprises a catheter connector component and a decoupling component, wherein the catheter connector component is configured to detachably couple with the catheter, wherein at least a lengthwise section of the fluid flow channel concentrically or eccentrically surrounds at least a lengthwise section of the liquid flow channel,
   wherein the liquid flow channel has a first tube connection piece, wherein the fluid flow channel has a second tube connection piece, wherein the second tube connection piece surrounds the first tube connection piece, wherein between the first tube connection piece and the second connection piece tube is an annular gap that provides for at least a part of the fluid flow channel, and wherein the second tube connection piece protrudes inside the flared part of the funnel-shaped part,
   wherein the coupling component is adapted for coupling at least the respective first tube connection piece of the catheter in liquid communication with the injection liquid reservoir via a respective first tube, and
   the second tube connection piece of the catheter in liquid communication with a fluid reservoir via a respective second tube, and
   wherein the fluid reservoir is the injection liquid reservoir.

2. The assembly according to claim 1, wherein the first tube connection piece protrudes beyond the funnel-shaped part.

3. The assembly according to claim 1, wherein the second tube connection piece protrudes beyond the funnel-shaped part.

4. The assembly according to claim 1, wherein none of the first tube connection piece or the second tube connection piece protrude beyond the funnel-shaped part.

5. The assembly according to claim 1, wherein the first tube connection piece and the second tube connection piece are configured as a first coupling means inside an opening of the funnel-shaped part.

6. The assembly according to claim 1, wherein at least one of the first tube connection piece or the second tube connection piece is made of an elastic and/or flexible material.

7. The assembly according to claim 1, wherein at least one of the first tube connection piece and second tube connection piece is rigid.

8. The assembly according to claim 1, wherein the liquid flow channel and the fluid flow channel are substantial parallel flow channels.

9. The assembly according to claim 1, wherein at least a length of the liquid flow channel at the funnel-shaped part extends inside the fluid flow channel.

10. The assembly according to claim 1, wherein the first tube connection piece has a different cross-section than the second tube connection piece.

11. The assembly according to claim 1, wherein a size of the at least one injection opening and/or the at least one delivery opening is at least about 50% or more of a cross-section of a corresponding flow channel.

12. An apparatus adapted for injection of liquid into a body cavity, comprising the assembly according to claim 1.

13. The apparatus according to claim 12, wherein the coupling component has a first flow connector adapted to fluid-tight fit together with the first tube connection piece.

14. The apparatus according to claim 13, wherein the coupling component has a second flow connector adapted to fluid-tight fit together with the second tube connection piece.

15. The apparatus according to claim 14, wherein the first flow connector and the second flow connector have no threading.

16. The apparatus according to claim 14, wherein a third flow channel extends through the coupling component from the first flow connector to a first coupling opening or a first coupling piece for coupling to a first tube of the tubes, and a fourth flow channel extends through the coupling component from the second flow connector to a second coupling opening or a second coupling piece for coupling to a second tube of the tubes.

17. The apparatus according to claim 16, wherein the third flow channel and the fourth liquid low channel of the coupling component are substantially straight.

18. The apparatus according to claim 16, wherein the catheter connector component has a first catheter connector part end opposite a second catheter connector part end, and the decoupling component is adapted to release the tube connection component from the catheter connector component.

19. The apparatus according to claim 18, wherein the first catheter connector part end is adapted to couple together with the catheter and the second catheter connector part end opposite to the first catheter connector part end is adapted for coupling together with the tube connection component.

20. The apparatus according to claim 19, wherein the catheter and/or the coupling component and/or the tube coupling adaptor is made in a single step by 1K injection molding, 2K injection molding or 3K injection molding.

21. The apparatus according to claim 18, wherein the tube connection component has a tubular front end part adapted to couple together with the second catheter connector part end and/or to the catheter, and an opposite tube connecting end part adapted to be coupled with the tubes and/or the decoupling component.

22. The apparatus according to claim 21, wherein the decoupling component is displaceable along a longitudinal axis of the tube coupling adaptor to release the tube connection component from the catheter connector component.

23. The apparatus according to claim 21, wherein the tubular front end part has an exterior tubular coupling piece that surrounds an interior tubular coupling piece to define a flow gap in-between said coupling pieces.

24. The apparatus according to claim 23, wherein the tube connection component has a guide plate member disposed between the tubular front end part and the tube connecting end part, which guide plate member is provided with openings arranged to direct fluid flowing inside the flow gap along the fourth flow channel of a second coupling piece of the tube connecting end part, and liquid flowing into the interior tubular coupling piece into the third flow channel of a first coupling piece of the tube connecting end par, which the first coupling piece and second coupling piece are adapted to couple with tubes.

25. The apparatus according to claim 1, wherein the apparatus further comprises a valve means and a pump means inserted between said first tube and/or second tube and said injection liquid reservoir and/or said fluid reservoir for pumping the liquid from said injection liquid reservoir and/or pumping the fluid from the fluid reservoir of the liquid into the expandable fixation member and out of the free end of the elongate tubular catheter part, respectively.

26. The assembly according to claim 1, wherein the catheter connector component, the coupling component, and the decoupling connector are detachable from each other.

27. The assembly according to claim 1, wherein at least a portion of an exterior annular wall of the second tube connection piece has a uniform outer diameter along a longitudinal axis of the second tube connection piece from a most distal end portion of the second tube connection piece.

28. An assembly comprising a catheter and a coupling component, which catheter is adapted for injection of a liquid into a body cavity, said catheter being coupled to the coupling component adapted to couple to tubes for establishing fluid communication to an injection liquid reservoir, said catheter has
a main body comprising a funnel-shaped part delimited by an annular funnel wall and an elongate tubular catheter part delimited by an annular catheter wall, which funnel-shaped part has a flared part that, via a smooth transition, tapers into a tapering part, which extend into the elongate tubular catheter part,
the main body accommodates a liquid flow channel, which is adapted to expel the liquid via at least one injection opening in a free end of the elongate tubular catheter part opposite the funnel-shaped part, and
an expandable fixation member that surrounds an elongate fixation section of the elongate tubular catheter part a distance from the free end of said elongate tubular catheter part, and a fluid flow channel which is adapted to, via at least one delivery opening provided in the elongate fixation section of the elongate tubular catheter part, deliver a fluid to the expandable fixation member,
wherein the assembly comprises a tube coupling adaptor, the coupling component is a tube connection component being part of the tube coupling adaptor, and which tube coupling adaptor further comprises a catheter connector component and a decoupling component, wherein the catheter connector component is configured to detachably couple with the catheter, wherein at least a lengthwise section of the fluid flow channel concentrically or eccentrically surrounds at least a lengthwise section of the liquid flow channel,
wherein the liquid flow channel has a first tube connection piece, wherein between the first tube connection piece and the second connection piece tube is an annular gap that provides for at least a part of the fluid flow channel, wherein the fluid flow channel has a second tube connection piece, and wherein none of the first tube connection piece or the second tube connection piece protrude beyond the funnel-shaped part.

29. An assembly comprising a catheter and a coupling component, which catheter is adapted for injection of a liquid into a body cavity, said catheter being coupled to the coupling component adapted to couple to tubes for establishing fluid communication to an injection liquid reservoir, said catheter has
a main body comprising a funnel-shaped part delimited by an annular funnel wall and an elongate tubular catheter part delimited by an annular catheter wall, which funnel-shaped part has a flared part that, via a smooth transition, tapers into a tapering part, which extend into the elongate tubular catheter part,
the main body accommodates a liquid flow channel, which is adapted to expel the liquid via at least one injection opening in a free end of the elongate tubular catheter part opposite the funnel-shaped part, and
an expandable fixation member that surrounds an elongate fixation section of the elongate tubular catheter part a distance from the free end of said elongate tubular catheter part, and a fluid flow channel which is adapted to, via at least one delivery opening provided in the elongate fixation section of the elongate tubular catheter part, deliver a fluid to the expandable fixation member,
wherein the assembly comprises a tube coupling adaptor, the coupling component is a tube connection component being part of the tube coupling adaptor, and which tube coupling adaptor further comprises a catheter connector component and a decoupling component, wherein the catheter connector component is configured to detachably couple with the catheter, wherein at least a lengthwise section of the fluid flow channel concentrically or eccentrically surrounds at least a lengthwise section of the liquid flow channel,
wherein the liquid flow channel has a first tube connection piece, wherein between the first tube connection piece and the second connection piece tube is an annular gap that provides for at least a part of the fluid flow channel, wherein the fluid flow channel has a second tube connection piece, wherein the coupling component is adapted for coupling
- at least the respective first tube connection piece of the catheter in liquid communication with the injection liquid reservoir via a respective first tube, and
- the second tube connection piece of the catheter in liquid communication with a fluid reservoir via a respective second tube, and wherein the fluid reservoir is the injection liquid reservoir.

* * * * *